(12) United States Patent
Vogt et al.

(10) Patent No.: US 11,511,073 B2
(45) Date of Patent: Nov. 29, 2022

(54) DEVICE FOR TEMPORARY LOCAL APPLICATION OF FLUIDS

(71) Applicant: Heraeus Medical GmbH, Wehrheim (DE)

(72) Inventors: Sebastian Vogt, Wehrheim (DE); Thomas Kluge, Wehrheim (DE)

(73) Assignee: Heraeus Medical GmbH, Wehrheim (DE)

( * ) Notice: Subject to any disclaimer, the term of this patent is extended or adjusted under 35 U.S.C. 154(b) by 362 days.

(21) Appl. No.: 16/666,630

(22) Filed: Oct. 29, 2019

(65) Prior Publication Data

US 2020/0129732 A1 Apr. 30, 2020

(30) Foreign Application Priority Data

Oct. 29, 2018 (DE) .................... 10 2018 218 429.1

(51) Int. Cl.
*A61M 25/00* (2006.01)
*A61M 39/10* (2006.01)
*A61M 39/24* (2006.01)

(52) U.S. Cl.
CPC .... *A61M 25/0029* (2013.01); *A61M 25/0043* (2013.01); *A61M 39/10* (2013.01);
(Continued)

(58) Field of Classification Search
CPC .......... A61M 25/0029; A61M 25/0043; A61M 39/10; A61M 39/24; A61M 2025/0004;
(Continued)

(56) References Cited

U.S. PATENT DOCUMENTS 3,055,482 A 9/1962 Stenzel
4,186,745 A 2/1980 Kauzlarich et al.
(Continued)

FOREIGN PATENT DOCUMENTS

DE 3203957 8/1983
DE 3334595 4/1985
(Continued)

OTHER PUBLICATIONS

Von K. Klemm, "Gentamcin-PMMA-beads in treating bone and soft tissue infections", Zentralbl. Chir. 104 (14) (1979) 934-942.
(Continued)

*Primary Examiner* — Kevin C Sirmons
*Assistant Examiner* — Alexandra Lalonde
(74) *Attorney, Agent, or Firm* — Dicke, Billig & Czaja, PLLC

(57) ABSTRACT

One embodiment is a medical device with a flexibly deformable external hose. The external hose includes multiple openings, at least one of them arranged in a first end of the external hose. It includes a flexible internal hose, which is arranged on the inside of the external hose. The internal hose, in an expanded state, has an external diameter that is at least equal to the internal diameter of the external hose, closing the openings of the external hose. The external diameter of the internal hose can be transitioned from the expanded state into a radially contracted state, exposing the openings. A connection firmly connects the external hose and the internal hose on the first end of the external hose, and closes them in fluid-tight manner. A connector supplies the fluid into the intervening space between the external and the internal hose.

16 Claims, 14 Drawing Sheets

(52) U.S. Cl.
CPC ..... *A61M 39/24* (2013.01); *A61M 2025/0004* (2013.01); *A61M 2025/0008* (2013.01); *A61M 2025/0024* (2013.01); *A61M 2025/0057* (2013.01)

(58) Field of Classification Search
CPC .. A61M 2025/0008; A61M 2025/0024; A61M 2025/0057; A61M 2025/0018; A61M 25/0023; A61M 25/0015; A61M 25/0021; A61M 25/007; A61M 25/0071; A61M 25/0074; A61M 25/0028; A61M 25/00; A61M 25/003; A61M 2025/0079; A61M 2025/0006; A61M 2025/0025; A61M 2025/0035; A61M 2025/0039; A61M 2025/004
See application file for complete search history.

(56) References Cited

U.S. PATENT DOCUMENTS

| | | | |
|---|---|---|---|
| 4,291,013 A | | 9/1981 | Wahlig et al. |
| 5,792,118 A | * | 8/1998 | Kurth ................ A61M 25/0017 604/246 |
| 5,817,072 A | | 10/1998 | Lampropoulos et al. |
| 6,602,241 B2 | | 8/2003 | Makower et al. |
| 6,936,057 B1 | * | 8/2005 | Nobles ............. A61B 17/12036 606/194 |
| 8,090,430 B2 | | 1/2012 | Makower et al. |
| 2007/0135791 A1 | | 6/2007 | Slater et al. |
| 2007/0185380 A1 | | 8/2007 | Kucklick |
| 2009/0287147 A1 | | 11/2009 | Wenchell et al. |
| 2013/0085381 A1 | * | 4/2013 | Comerota ......... A61M 25/0074 600/424 |
| 2013/0204208 A1 | | 8/2013 | Olson et al. |
| 2014/0336617 A1 | * | 11/2014 | Schaeffer ............. A61B 5/1076 604/514 |
| 2015/0366462 A1 | * | 12/2015 | Ramos .................... A61B 5/01 600/549 |
| 2016/0220788 A1 | | 8/2016 | Comerota et al. |

FOREIGN PATENT DOCUMENTS

| | | |
|---|---|---|
| DE | 3429038 | 2/1986 |
| EP | 0 170 979 | 2/1986 |
| EP | 0 137 297 | 10/1986 |
| JP | 2002301161 | 10/2002 |
| JP | 2008509781 | 4/2008 |
| JP | 2013013740 | 1/2013 |
| JP | 2013128602 | 7/2013 |

OTHER PUBLICATIONS

Klaus-Dieter Kuehn, et al. "Lokale Antibiotikatherapie Der Unfallchirurg" 120 (2017), p. 561-572.
Klaus W. Klemm, "Antiobiotic Bead Chains", Clinical Orthopaedics, No. 295 (1993), p. 63-76.

* cited by examiner

DEVICE FOR TEMPORARY LOCAL APPLICATION OF FLUIDS

CROSS-REFERENCE TO RELATED APPLICATION

This Utility Patent Applications claims priority to German Application No. 10 2018 218 429.1 filed on Oct. 29, 2018, which is incorporated herein by reference.

TECHNICAL FIELD

One embodiment relates to a medical device for temporary local application of fluids, in particular of pharmaceutical fluids. One embodiment also relates to a hose system for setting up a device of this type, a method for shortening a hose system of this type or of a device of this type, and a method for operating a device of this type.

BACKGROUND

The local application of pharmaceutical agents, in particular of antibiotics, has been known for decades and is time-proven in particular in the treatment and/or mitigation of bone tissue infections. These agents can be subdivided into non-absorbable and absorbable and/or biodegradable drug carriers. However, supplying fluids into hollow spaces for the purpose of rinsing and disinfection can also be useful in the disinfection and cleaning of medical devices having hollow spaces that would otherwise be difficult to access.

Absorbable and non-absorbable drug carriers for medical treatment of infections in hollow spaces and cavities that are difficult to access, such as bone cavities, are known.

Examples of non-absorbable drug carriers include the bead chains that have been known by the trade name of Septopal® since 1977. These consist of polymethylmethacrylate beads containing the broadband antibiotic gentamicin sulfate, whereby these beads are arranged in the form of chains on threads of steel (K. Klemm: Gentamcin-PMMA-beads in treating bone and soft tissue infections. Zentralbl. Chir. 104(14) (1979) 934-942; K. Klemm: Antibiotic bead chains. Clin. Orthop. 295 (1993) 63-76). This chain-like drug carrier (Septopal®) is time-proven over the course of decades in the local antibiotic treatment of osteomyelitis.

It is advantageous in this context that the gentamicin sulfate is released from the drug carrier in substantial quantities over a period of time of several days. It is also advantageous that the chain-like drug carrier can be readily adapted to the anatomical situation at the implantation site by the medical user by simply cutting off the thread of steel with excessive beads. It is disadvantageous that the drug carrier contains gentamicin sulfate exclusively and that the medical user cannot modify the drug carrier to include other antibiotics in accordance with the sensitivity of the microbial germs. Moreover, the release of the pharmaceutical agent can no longer be adapted to the course of treatment without exchanging the bead chain once the bead chain is implanted. As a result, especially the successful local treatment of infections by problematic germs, such as MRSA and VRSA, is feasible only to a limited degree or not at all. Removing the bead chains after successful release of the agent is associated with significant stress for the patients since the bead chains grow onto the connective tissue.

Non-woven materials and sponges made of collagen or gelatin are examples of absorbable and/or biodegradable drug carriers. For exemplary purposes, printed specifications DE 34 29 038 A1, DE 33 34 595 A1, DE 28 43 963 C2, DE 32 03 957 C2, and DE 33 34 595 A1 shall be cited in this context. These contain gentamicin sulfate or mixtures of gentamicin sulfate and a poorly water-soluble gentamicin salt. Moreover, a multitude of absorbable and/or biodegradable drug carriers based on tricalcium phosphate, hydroxylapatite, gypsum, and mixtures thereof as well as composite materials of the salts and organic binding agents are available. An overview has been published by Kühn et al. (K.-D. Kühn, N. Renz, A. Trampuz: Lokale Antibiotika-Therapie (Local antibiotics therapy). Der Unfallchirurg. 120 (2017) 561-572).

It is a disadvantage of the listed non-absorbable and absorbable and/or biodegradable drug carriers that the antimicrobial drug is fixed by the selected composition and that the drug can no longer be exchanged or supplemented by other drugs after implantation of the drug carrier. Moreover, the drug release of all previous local drug release systems is based on diffusion such that high amounts of drug are released only in the first hours or days at most. One exception to this rule is the use of poorly water-soluble drug salts, in which the drug release depends on the solubility equilibrium of the drug salts.

It is therefore desirable to have a drug carrier that permits local application of any pharmaceutical agent and allows the pharmaceutical agent to be replaced at any time by other fluid pharmaceutical agents. It is also desirable to be able to directly set, from outside, the drug concentration attained right at the site of implantation.

SUMMARY

One embodiment is a medical device for local application of a fluid, including a flexibly deformable external hose with a hose wall, wherein the external hose comprises multiple through-going openings in the hose wall, wherein at least one of the multiple through-going openings is arranged in the area of a first end of the external hose. It includes a flexible internal hose, wherein at least sections of the internal hose are arranged on the inside of the external hose, where by the internal hose, in an expanded state, has an external diameter that is at least equal to the internal diameter of the external hose, such that the internal hose, in the expanded state, closes the through-going openings of the external hose on the internal side of the external hose, wherein the external diameter of the internal hose can be transitioned from the expanded state into a radially contracted state, in which the internal hose has a smaller external diameter, such that the openings are being exposed. It includes a connection that firmly connects the external hose and the internal hose to each other on the first end of the external hose, and closes them in fluid-tight manner and a connector for supplying the fluid into the intervening space between the internal side of the external hose and the external side of the internal hose, wherein the connector is arranged in the area of a second end of the external hose, wherein the second end of the external hose is situated opposite from the first end of the external hose.

BRIEF DESCRIPTION OF DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

Further exemplary embodiments shall be illustrated in the following on the basis of fourteen schematic figures, though without limiting the scope of the invention.

FIG. 13: illustrates two schematic perspective longitudinal cross-sectional views, sectioned perpendicular with respect to each other, of the first device according to FIGS. 1 and 5 to 12, whereby the openings in the external hose are closed again by pushing the thrust piston in.

DETAILED DESCRIPTION

Figure 1:
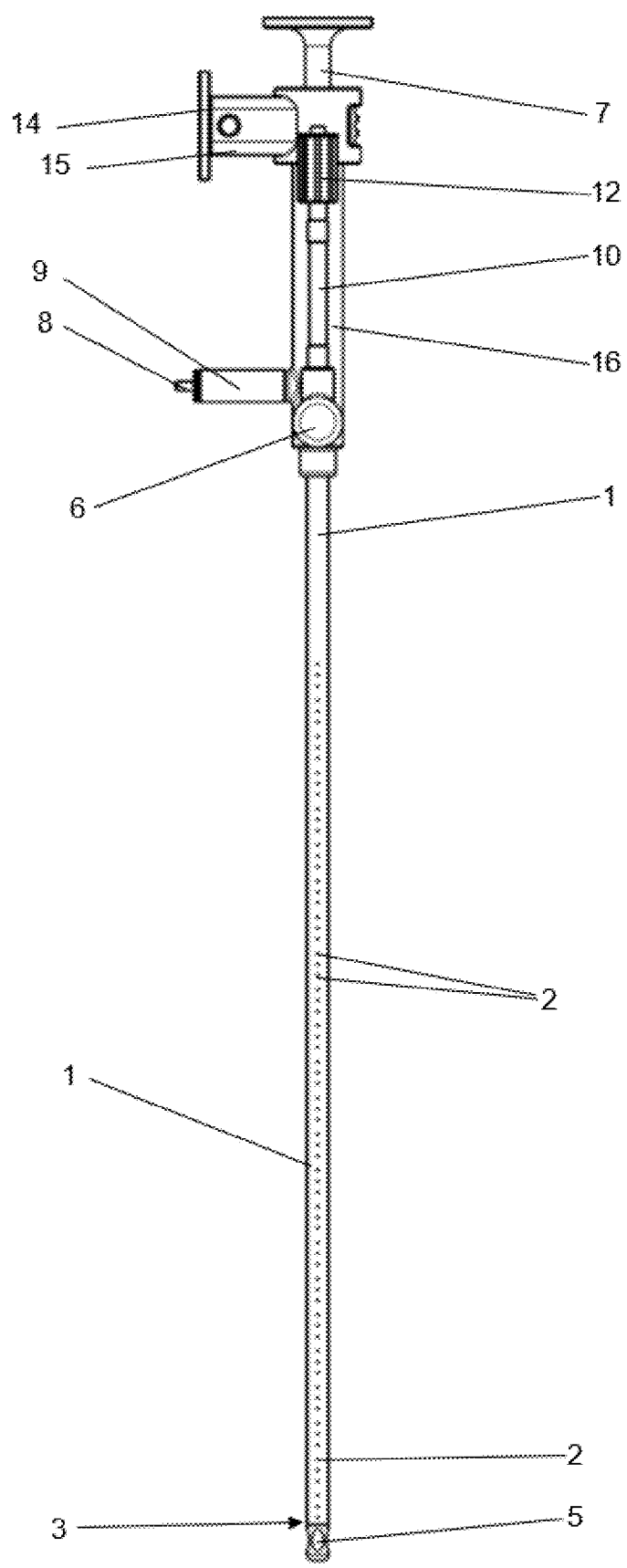
FIG. 1: illustrates a schematic view of an exemplary first medical device according to one embodiment for local application of a fluid.

In the following Detailed Description, reference is made to the accompanying drawings, which form a part hereof, and in which is illustrated by way of illustration specific embodiments in which one embodiments may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present embodiments. The following detailed description, therefore, is not to be taken in a limiting sense, and the scope of the present embodiments are defined by the appended claims.

It is to be understood that the features of the various exemplary embodiments described herein may be combined with each other, unless specifically noted otherwise.

One embodiment is based on the object to provide a medical device for local application of fluids by means of which a local and temporary release of the fluid in areas that are difficult to access is made possible. The device shall be flexibly adaptable to different application areas in this context. Using it for treatment of an infection is to enable a very gentle treatment, in which the adjacent inflamed tissue is being irritated as little as possible both during the temporary release of the fluid and during the insertion and removal of the inserted part of the device. The device shall also be well-suited for repeated release of the fluid, including over extended periods of time, at a certain site without the device having to be removed for this purpose. The device shall be inexpensive to manufacture and should best be a hygienic disposable product for single use only. In this context, at least the part of the device to be placed in the hollow space to be rinsed or even the entire device should be inexpensive and easy to dispose of as a disposable product.

It is therefore also the object of one embodiment to develop a simple, inexpensive device for local application of fluids. The device is to make feasible a local application of pharmaceutical fluids of any composition, for example of antibiotic solutions. One part of the device is situated in the patient and a second part of the device is situated outside of the patient upon its medical use after an implantation. It shall be possible to introduce the pharmaceutical fluids into the part of the device that is situated outside of the patient and to supply them through the device to the site of implantation and to release them there. It shall be feasible to plastically deform the device in order to adapt it to the anatomical conditions at the implantation site or to the geometrical shape of the hollow form. The pharmaceutical fluids are to be released from openings that are arranged along the device. Ideally, the openings shall be reversibly closable in order to prevent connective tissue from growing into the device and/or to prevent coagulated blood from clotting the openings. Moreover, the device should be designed appropriately such that the part of the device situated in the patient can be adapted by shortening its length to the existing anatomical situation of the patient without the function of the device being impaired.

The objects of one embodiment are met by a medical device for local application of a fluid, comprising A) a flexibly deformable external hose with a hose wall, whereby the external hose includes multiple through-going openings in the hose wall, whereby at least one of the multiple through-going openings is arranged in the area of a first end of the external hose;

B) a flexible internal hose, whereby at least sections of the internal hose are arranged on the inside of the external hose, whereby the internal hose, in an expanded state, has an external diameter that is at least equal to the internal diameter of the external hose, such that the internal hose, in the expanded state, closes the through-going openings of the external hose on the internal side of the external hose, whereby the external diameter of the internal hose can be transitioned from the expanded state into a radially contracted state, in which the internal hose has a smaller external diameter, such that the openings are being exposed;

C) a connection that firmly connects the external hose and the internal hose to each other on the first end of the external hose, and closes them in fluid-tight manner; and D) a connector for supplying the fluid into the intervening space between the internal side of the external hose and the external side of the internal hose, whereby the connector is arranged in the area of a second end of the external hose, whereby the second end of the external hose is situated opposite from the first end of the external hose.

The device can also be used to rinse off or rinse out medical instruments, in particular medical instruments having hollow spaces into which the external hose can be introduced. But the device can also be used for freely distributing the fluid. However, a medical application of the device according to one embodiment, in which the external hose is introduced into a cavity of a human body and the fluid is used for treating the adjacent tissue is preferred in one embodiment.

At least two or more through-going openings are arranged in the lateral hose wall of the external hose. By this means, the external hose with the internal hose can be shortened at least once even if one of the through-going openings is thus removed, without none of the remaining openings still being exposed after shortening.

The external hose is closed in fluid-tight manner on the first end of the external hose. The through-going openings connect the inside of the external hose to the outer surroundings of the external hose.

The hose wall of the external hose is the lateral wall of the external hose that surrounds all sides.

The lateral hose wall is the jacket surface of the external hose and of the internal hose as well. Accordingly, the lateral hose wall is the entire jacket that connects the two ends (the first end and the second end) of the respective hose. In the case of straight hoses with a cylindrical geometry, the jacket surface is the wall perpendicular to the cylinder axis of the cylindrical hose. Accordingly, the through-going openings are situated in the jacket surface.

One embodiment preferably provides the internal hose to close the external hose on the first end of the external hose.

In one embodiment, at least one of the multiple through-going openings is arranged at a distance of up to 1.5 cm from the first end of the external hose. Preferably in one embodiment, at least one of the multiple through-going openings is arranged at a distance of up to 5 mm from the first end of the external hose. By this means, it can be ensured that even the part of the hollow space to be rinsed, on which the tip with the first end of the external hose is arranged, can be accessed by the fluid and is thus accessible to a rinsing effect or a medical treatment.

In one embodiment, the connector is arranged at a distance of up to 5 cm from the second end of the external hose. In one embodiment, the connector is arranged at a distance of up to 2 mm from the second end of the external hose. By this means, the device does not need to be excessively long in design and the connector is easily accessible from outside even when the external hose is introduced deeply into a cavity or a hollow space.

The internal hose is preferred to be radially deformable. As a result, it can be transitioned from the contracted state into the expanded state without any wrinkling occurring.

The fluid can be applied through the connector and through the intervening space between the internal side of the external hose and the external side of the internal hose through the multiple through-going openings in the external hose, when the internal hose is in the contracted state. Accordingly, as soon as the internal hose is in the contracted state, there is a connection extant that is permeable to the fluid in the form of an intervening space between the hoses, between the connector and the through-going openings, through which the fluid can be applied.

The connector can be a connector shaped as a tee on the external hose or on a hollow space connected to it, but can just as well be implemented simply by means of the second end of the external hose through which the fluid can be supplied.

In one embodiment, the internal hose must be guided through the wall of the external hose in the area of the second end of the external hose or through a termination of the external hose on the second end of the external hose.

In one embodiment, the expanded state is the relaxed state of the internal hose, whereas the radially contracted state of the internal hose needs to be maintained in the radially contracted state through the action of a force, such as a negative pressure or a suction. This is advantageous in that the through-going openings in the external hose are closed in the relaxed state. By this means, the openings cannot stay open inadvertently and cannot open up, when the internal hose relaxes because (internal) forces diminish.

The first end of the external hose can also be referred to as the distal end of the external hose. For purposes of simplicity, the first end of the external hose also defines the first end (including the distal end) of the internal hose. Accordingly, the second end of the external hose facing the connector and the user is the proximal end of the external hose.

One embodiment can provide the internal hose to be transitioned into the radially contracted state through the generation of a negative pressure on the inside of the internal hose or through a volume reduction of a liquid on the inside of the internal hose.

By this means, the multiple through-going openings in the external hose can be reliably opened by mechanical means through the generation of the negative pressure or the volume reduction in the internal hose. Moreover, the through-going openings in the external hose are closed again automatically, when the internal hose expands again into the expanded state. This allows the through-going openings in the external hose to be exposed easily and rapidly. In particular, the external shape of the external hose is neither changed nor deformed, when the through-going openings are being opened, such that any irritation of the adjacent tissue by the opening process is minimised.

Moreover, one embodiment can provide the internal hose to be guided through a closure of the external hose on the second end of the external hose or through the lateral hose wall of the external hose in the area of the second end.

By this means, the internal hose is accessible from outside such that the pressure on the inside of the internal hose and/or the volume of the internal hose can be manipulated from outside in order to transition the internal hose from the expanded into the radially contracted state, and vice versa.

In this context, one embodiment can provide an operating facility to be fastened to an end of the internal hose that is guided through the closure or the hose wall of the external hose, whereby the pressure of a gas inside the internal hose can be changed or the volume of a liquid inside the internal hose can be changed by the operating facility, and the internal hose can be transitioned from the expanded into the radially contracted state through reduction of the pressure of the gas or reduction of the volume of the liquid.

By this means, the expanded state and the radially contracted state of the internal hose can be set easily by mechanical means.

A development of one embodiment can provide the device to include an operating facility, in particular to include a piston syringe, a pump or a pipetting ball as operating facility, by means of which the internal hose can be transitioned inside the external hose from the expanded state into the radially contracted state such that the openings in the external hose are being opened. By this means, the device can easily be operated from outside, meaning that the internal hose can be transitioned from the expanded state into the radially contracted state and from the radially contracted state into the expanded state.

Piston syringes are preferred in this context according to one embodiment. Referring to the use of a piston syringe as operating facility, one embodiment provides a thrust piston of the piston syringe to be lockable by a detachable locking mechanism.

In one embodiment, the connection can be implemented by a connecting element.

By this means, a variable connection can be used, since the connecting element can be repositioned and can be fastened to a newly produced distal first end of the hoses after the hoses have been shortened.

In this context, one embodiment can provide the connecting element to include a conical or cylindrical projection that is plugged or screwed into the internal hose such that the internal hose is widened appropriately by the projection in the area of the first end of the external hose such that the internal hose closes the external hose on the first end of the external hose in fluid-tight manner.

This allows the distal (first) ends of the hoses to be sealed and connected reliably.

Moreover, in this context, one embodiment can provide the connecting element to be connected in detachable manner to a first end of the external hose and/or to the internal hose.

Both measures allow a variable connection to be used such that the hose can be shortened to various lengths and the connection can be established easily by the user plugging or screwing the connecting element in. By this means, the device can be adapted by the user to different applications or treatment scenarios.

One embodiment can just as well provide the connecting element to include a first rotationally symmetrical body with an external thread or with fins on the outside, whereby the external thread or the rotationally symmetrical body includes an external diameter that is larger than the internal diameter of the internal hose.

By this means, the connection can be repositioned after the hoses are shortened and, in the process, the first end of the external hose and the internal hose can be sealed at this site by the connecting element.

In this context, one embodiment can provide the connecting element to include a second rotationally symmetrical body that has an external diameter that is smaller than or equal to the external diameter of the external hose, whereby the first rotationally symmetrical body and the second rotationally symmetrical body are axially connected to each other, and whereby the second rotationally symmetrical body is preferred to be at least 5 mm in length in axial direction of the connecting element.

This makes sure that the connecting element can be grasped by hand and can be plugged or screwed in by hand in order to establish the connection.

According to a preferred development, one embodiment can provide the connecting element to be screwed or pressed into the internal hose on the side of the first end of the external hose and to fully close the entire free cross-section of the internal hose in fluid-tight or fluid tight and gas-tight manner, whereby the internal hose thus closed is pressed appropriately against the internal side of the external hose such that the external hose is closed on the first end by the internal hose in liquid-tight and gas-tight manner.

What this attains is that both hose ends on the first end of the external hose are being closed in simple manner by the connecting element, and thus implement the connection. By this means, the internal and the external hose can be shortened, whereby the connecting element is being closed by screwing or pressing it into the new end generated by cutting. By this means, the device can be easily adapted to the respective treatment scenario. Due to the external hose being closed on the first end by the internal hose in liquid-tight and gas-tight manner, having the connecting element makes sure that there is no hollow space present between the external side of the internal hose and the internal side of the external hose along the axial extension of the connecting element.

Moreover, one embodiment can provide the intervening space between the external hose and the internal hose to be closed in fluid-tight manner on the second end of the external hose.

By this means, the fluid is prevented from being able to exit at sites other than the through-going openings. The intervening space between the external hose and the internal hose is then closed toward the outside in fluid-tight manner except for the through-going openings in the hose wall of the external hose and except for the connector. The fluid can then be supplied only through the connector and can be released only through the through-going openings, if the latter are opened.

Moreover, one embodiment proposes the external hose to surround the internal hose on its first end.

By this means, the internal hose can be used to seal the external hose on the first end of the external hose. In one embodiment, the external hose surrounds the internal hose on its second end as well.

One embodiment can provide the internal hose to contain a gas, whereby the internal hose can be transitioned into the radially contracted state by reducing the pressure of the gas in the internal hose and can be transitioned again into the expanded state by again supplying the gas or a gas, or can provide a liquid to fill the internal hose, whereby the internal hose can be transitioned into the radially contracted state by aspirating a portion of the liquid from the internal hose and can be transitioned again into the expanded state by again supplying the liquid or another liquid into the internal hose.

By this means, aspiration and pushing in of a gas or a liquid from and into the internal hose allows the expanded state and the radially contracted state to be set and thus allows the multiple through-going openings in the external hose to be opened and closed. Theoretically, a mixture of gas and liquid can just as well be present on the inside of the internal hose and can be used for setting the expanded and the radially contracted states.

One embodiment can provide for an operating facility for aspiration of the gas or liquid from the internal hose to be connected to the internal hose such that the internal hose can be transitioned into the radially contracted state by aspiration of the gas or liquid and such that the openings in the external hose thus open.

The operating facility for aspiration of the gas or liquid can in one embodiment be a negative pressure-generating facility, such as, for example, a thrust piston, a piston syringe, a pump or a pipetting ball, that is axially mobile in a swept volume.

The "operation" of the internal hose and/or the opening and closing of the through-going openings is being simplified by this means.

Devices according to one embodiment can also be characterised in that the internal side of the external hose and the external side of the internal hose jointly form a valve.

By this means, it is made clear that the through-going openings in the external hose can be closed completely by the internal hose.

In this context, one embodiment can provide the valve to be opened by reducing a gas pressure on the inside of the internal hose or by aspirating a liquid from the inside of the internal hose, and through a resulting radial contraction of the internal hose.

A simple way of operating the valve by means of a pressure change in the internal hose is being provided by this means.

Moreover, one embodiment can provide that at least one of the elements selected from the connection, the external hose, and the internal hose includes a radiopaque material or consists of a radiopaque material, whereby the radiopaque material is in one embodiment selected from stainless steel, titanium, titanium alloys, tantalum, tantalum alloys, barium sulfate-containing plastics, and zirconium dioxide-containing plastics or combinations thereof.

By this means, the positioning of the external hose and/or of the internal hose and, if applicable, of the connection in the body of a patient can be recognized easily in radiographs. For this purpose, it is advantageous in one embodiment, in the case of the external and the internal hose, to have the radiopaquer be distributed and/or arranged along the longitudinal axis of the respective hose. Obviously, the connecting element, if one is present, is made up from or with one of the materials, stainless steel, titanium, titanium alloys, tantalum, tantalum alloy(s) or combinations thereof, whereas the internal hose and/or the external hose is/are mainly made up from or with barium sulfate-containing plastics and zirconium dioxide-containing plastics or combinations thereof.

Moreover, one embodiment can provide all, or pairs or groups of the multiple through-going openings to be situated at a distance from each other in axial direction of the external hose.

By this means, the fluid can exit at various sites that are situated at an axial distance from each other. Moreover, the external and the internal hose can be shortened in length at various sites, whereby at least one of the multiple through-going openings in the external hose is still present.

Moreover, one embodiment can provide water, a physiological saline solution or a Ringer solution or air to be arranged on the inside of the internal hose, whereby the internal hose can be transitioned into the radially contracted state by reducing the pressure of the air or the volume of the water, physiological saline solution or Ringer solution. By this means, the through-going openings can be opened in simple manner.

According to a particularly preferred development, one embodiment can provide an indicator to be connected to the internal hose that can be read from outside the device and indicates, whether the internal hose is in the expanded state or in the contracted state, whereby the indicator is preferred to be a negative pressure indicator that is connected to the internal hose in gas-permeable manner.

By this means, the user can easily recognise and determine, whether or not the internal hose is in the radially contracted state, and thus, whether the through-going openings in the external hose are open or closed.

For preservation of the elasticity of the internal hose, one embodiment can provide at least one metal wire or at least one metal coil to be arranged in the wall of the internal hose, whereby the at least one metal wire or the at least one metal coil is in one embodiment arranged along the entire length of the internal hose.

This ensures the elasticity of the internal hose even if the internal hose is repeatedly transitioned into the radially contracted state. This prevents the internal hose, even upon very frequent contraction of the internal hose, from being able to expand again subsequently in order to again close the through-going openings in the external hose.

In order to prevent contamination of the fluid, one embodiment can provide a non-return valve to be arranged in the connector or in a connection of the connector to the intervening space between the external hose and the internal hose, whereby the non-return valve prevents the fluid from flowing out of the intervening space into the connector or out of the connector.

By this means, spent fluid is prevented from being able to flow back into a fluid reservoir that is connected to the connector and from thus soiling or contaminating the reservoir.

One embodiment, one embodiment can provide at least sections of the internal hose to be arranged coaxially on the inside of the external hose.

Alternatively, the internal hose can just as well be firmly connected to the external hose in individual spots or all along a connection line. However, the internal hose is preferred not to be firmly connected to the external hose. Having a coaxial arrangement allows the through-going openings to be implemented on the entire circumference of the external hose. Moreover, this simplifies the installation of the device.

In order to maintain the pressure of the fluid in the entire intervening space between the external hose and the internal hose, one embodiment can provide the sum of the free cross-sections of the through-going openings in the external hose to be equal to or smaller than the cross-section of the intervening space between the internal wall of the external hose and the external wall of the internal hose in the radially contracted state.

By this means, the fluid can exit from all openings along the external hose when a pressure is applied to the intervening space between the internal wall of the external hose and the external wall of the internal hose.

The underlying objects of the present invention are also met by a hose system for setting up a device according to one embodiment, comprising a flexibly deformable external hose with a hose wall, whereby the external hose includes multiple through-going openings in the hose wall, and a flexible internal hose, whereby at least sections of the internal hose are arranged on the inside of the external hose, whereby the internal hose, in an expanded state, has an external diameter that is at least equal to the internal diameter of the external hose, such that the internal hose, in the expanded state, closes the through-going openings of the external hose on the internal side of the external hose, whereby the external diameter of the internal hose can be transitioned from the expanded state into a radially contracted state, in which the internal hose has a smaller external diameter, such that the openings are being exposed.

The hose system can be used to set up a device according to one embodiment, by connecting it to the other elements and by establishing the connection between the external and the internal hose at a first end of the external hose.

The underlying objects of the present invention are also met by a method for shortening and closing of a hose system of this type or of the internal hose and the external hose of a device according to one embodiment, characterised by shortening, in particular by cutting off, of the external hose and the internal hose starting from an originally first end of the external hose, such that these form a new joint first end, and subsequently screwing or pressing a connecting element into the open first end of the internal hose on the first end of the hose, such that the entire free cross-section of the internal hose is being closed completely in fluid-tight or fluid-tight and gas-tight manner, whereby the internal hose thus closed is being pressed, by its surface, against the internal side of the external hose, such that the external hose is being closed on the first end by the internal hose in liquid-tight and gas-tight manner.

This ensures that the fluid cannot exit on the first end of the external hose and that the pressure in the internal hose or the volume of the internal hose can be changed.

In one embodiment, the connecting element is being screwed or pressed in manually.

After the external hose is shortened, it can be sufficient to have just one through-going opening of the multiple through-going openings in the external hose remaining and being accessible to the fluid through the intervening space between the internal hose and the external hose.

The objects underlying the present invention are also met by a method for operating a device according to one embodiment, comprising the following steps of
A) transitioning the internal hose from the expanded state into the contracted state, whereby the openings in the external hose are thus being opened; and
B) supplying the fluid into the intervening space between the external hose and the internal hose.

In this context, one embodiment can provide the transitioning of the internal hose from the expanded state into the contracted state in step A) to take place by reducing the pressure of a gas on the inside of the internal hose or by reducing the volume of a liquid on the inside of the internal hose, whereby the external diameter of the internal hose is thus being reduced and the multiple openings in the hose wall of the external hose are thus being exposed.

By this means, the switching between the contracted state and the expanded state can take place in simple and reliable manner.

In turn, one embodiment can provide the gas or a gas or the liquid or a liquid to be supplied into the internal hose after step B) and thus the internal hose to be expanded and thus the multiple openings of the external hose to be closed again.

By this means, the method is well-suited for temporary supply or leakage of the fluid.

One embodiment can just as well provide a method for shortening and closing of a hose system according to one embodiment or of the internal hose and the external hose of a device according to one embodiment to be performed ahead of step A), wherein, by shortening, in particular by cutting off, of the external hose and of the internal hose starting from an originally first end of the external hose, a new joint first end is formed by them, and subsequently screwing or pressing a connecting element into the open first end of the internal hose on the first end of the hose, such that the entire free cross-section of the internal hose is being closed completely in fluid-tight or fluid-tight and gas-tight manner, whereby the internal hose thus closed is being pressed, by its surface, against the internal side of the external hose, such that the external hose is being closed on the first end by the internal hose in liquid-tight and gas-tight manner.

One embodiment is based on finding, surprisingly, that having an internal hose, whose radial circumference can be changed, allows the openings present in the hose wall of an external hose to be opened and closed reversibly for temporary release of a fluid. The openings can be closed or opened by simply expanding and contracting the internal hose. Concurrently, no forces are applied to the external hose that would lead to a strong deformation of the external hose. By this means, the external hose remains dimensionally stable. A mechanical stress on the adjoining surfaces to be treated by the fluid is thus prevented. The valve provided this way can thus be opened and closed again without changing the external shape of the external hose. By this means, for example, a mechanical irritation of an adjoining inflamed tissue can be prevented or at least reduced. Concurrently, the hose system can be shortened without any difficulty and its length can thus be adapted to the scenario at hand. For this purpose, it is only necessary to close the distal (first) end of the two hoses with an existing or new connecting element or a different connection, such as a connection generated by welding. The device and the hose system can be manufactured inexpensively from plastics and can thus be provided as a hygienic product for single use. In this context, the openings in the external hose are being closed appropriately such that, in the closed state, no undercuts arise in the intervening space between the external hose and the internal hose into which tissue might grow and which might thus render the device and/or the external hose more difficult to remove.

The medical device possesses a valve function that is to be operated outside the patient. Depending on the anatomical situation of the implantation site or depending on the depth of the hollow space, the device according to one embodiment can be adapted in size by simple mechanical shortening without any loss of function occurring.

The special advantage of the device according to one embodiment is that the medical user can apply an exactly defined volume of any fluid.

In the case of drug-containing fluids, one or more pharmaceutical agents in the fluid can be set to exactly predetermined concentrations. This allows exactly defined drug concentrations to be attained and used for treatment in the immediate vicinity of the openings of the device. It is another advantage of the device that the openings in the external hose are opened only during the application and are being closed thereafter, such that no blood or tissue fluid and no newly forming connective tissue can penetrate into the intervening space between the hoses of the device and form undercuts there, which might tear upon removal of the device and thus cause new irritation of the just previously treated tissue. Moreover, clogging of the device, in particular of the openings in the external hose, is prevented effectively. While the valve is being closed, the elastic restoring force of the internal hose extrudes residual fluid out of the intervening space through the openings into the surroundings of the external hose. No residues of the fluid remain in the device.

An exemplary device according to one embodiment for local application of fluids having a valve function is composed of a) a plastically deformable external hose with a first and a second hose end-piece, whereby the external hose possesses multiple openings in the jacket surface that connect the internal space of the external hose to the surroundings, whereby at least one of the openings is arranged in the vicinity of the first hose end-piece of the external hose;
b) an elastically deformable internal hose, with a first and a second hose end-piece, with an external diameter that is equal to or larger than the internal diameter of the external hose, that is arranged coaxially in the internal space of the external hose, and that closes the openings of the external hose, whereby the external hose surrounds the internal hose on the first hose end-piece of the internal hose;
c) a second fluid (liquid or gas) that fills the hollow space in the internal hose;
d) a negative pressure-generating device that is connected to the second hose end-piece of the internal hose;
e) a connector, in which the internal hose is guided out of the second hose end-piece of the external hose, whereby the connector is connected to the internal space of the external hose in fluid-permeable and gas-permeable manner,
f) a connecting element as closure that closes the first hose end-piece of the external hose and the first hose end-piece of the internal hose in fluid-tight and gas-tight manner; and
g) whereby the internal side of the external hose and the external surface of the internal hose jointly form a valve that can be opened by removing the second fluid from the internal space of the internal hose through the action of a negative pressure-generating device while contracting the internal hose perpendicular to the longitudinal axis of the internal hose.

The (first) fluid dispensed with the device is preferred to be a pharmaceutical fluid. The term, "pharmaceutical fluid", shall be understood to refer to aqueous and also to non-aqueous solutions or suspensions of pharmaceutical agents. Moreover, the term, "pharmaceutical fluid", shall be understood to also include mixtures and solutions of gases in water, water-containing liquids, and non-aqueous liquids. Accordingly, the term, "pharmaceutical fluid", also includes gases and gas mixtures.

The connecting element is composed, for example, of a first rotationally symmetrical body with an external thread, whereby the external thread possesses an external diameter that is larger than the internal diameter of the internal hose, and of a second rotationally symmetrical body with an external diameter that is smaller than or equal to the external diameter of the external hose, whereby the axial extension of the second rotationally symmetrical body is at least 5 mm, and whereby the first rotationally symmetrical body is axially connected to the second rotationally symmetrical body.

In a further alternative embodiment, an exemplary connecting element is composed of a first rotationally symmetrical body with fins running along the circumference, whereby the fins possess an external diameter that is larger than the internal diameter of the internal hose, and of a second rotationally symmetrical body with an external diameter that is smaller than or equal to the external diameter of the external hose, whereby the axial extension of the second rotationally symmetrical body is at least 5 mm, and whereby the first rotationally symmetrical body is axially connected to the second rotationally symmetrical body.

An exemplary method for shortening and closing the device can be characterised by the following steps proceeding in the stated order:
a) cutting off the internal hose and the external hose starting from the first (distal) hose end-pieces; and
b) screwing the connecting element, as a closure, into the newly generated first hose end-piece of the internal hose, whereby the internal space of the external hose is being closed in liquid-tight and gas-tight manner, whereby the expanding internal hose is concurrently being pressed, by its surface, on the first hose end-piece against the internal side of the external hose on the first hose end-piece, and the intervening space between the external side of the external hose and the internal side of the internal hose on the first hose end is being closed in liquid-tight and gas-tight manner.

Moreover, an exemplary method for opening of the valve of a device according to one embodiment for the application of fluids with the device and subsequent closing of the valve is characterised by the following steps proceeding in the stated order:
a) operating a negative pressure-generating facility in the internal hose;
b) aspirating the fluid or the gas in the internal space with the negative pressure-generating facility;
c) contracting the internal hose perpendicular to the longitudinal axis of the hose;
d) exposing an intervening space between the external side of the internal hose and the internal side of the external hose, whereby the openings of the external hose are being connected to the intervening space in fluid-permeable and gas-permeable manner;
e) pressing a fluid through the connector into the second hose end-piece into the intervening space between the external side of the internal hose and the internal side of the external hose;
f) fluid exiting from the openings in the external hose into the surroundings;
g) reducing the negative pressure in the internal hose by resetting the negative pressure-generating facility;
h) the liquid or the gas back-flowing out of the negative pressure-generating facility into the internal hose; and
i) elastic restoration of the internal hose while pressing the external side of the internal hose to the internal side of the external hose while closing the openings of the external hose.

Figure 2:
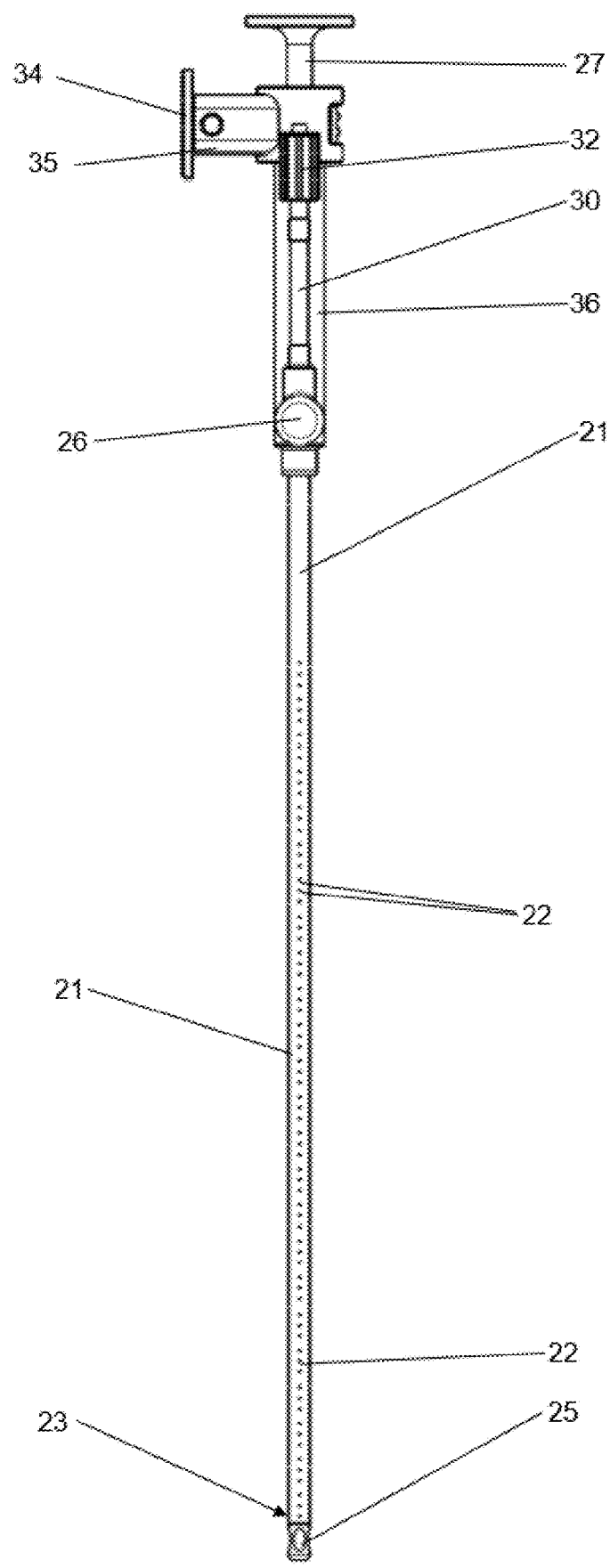
FIG. 2: illustrates a schematic view of an exemplary alternative second medical device according to one embodiment for local application of a fluid.
Figure 3:
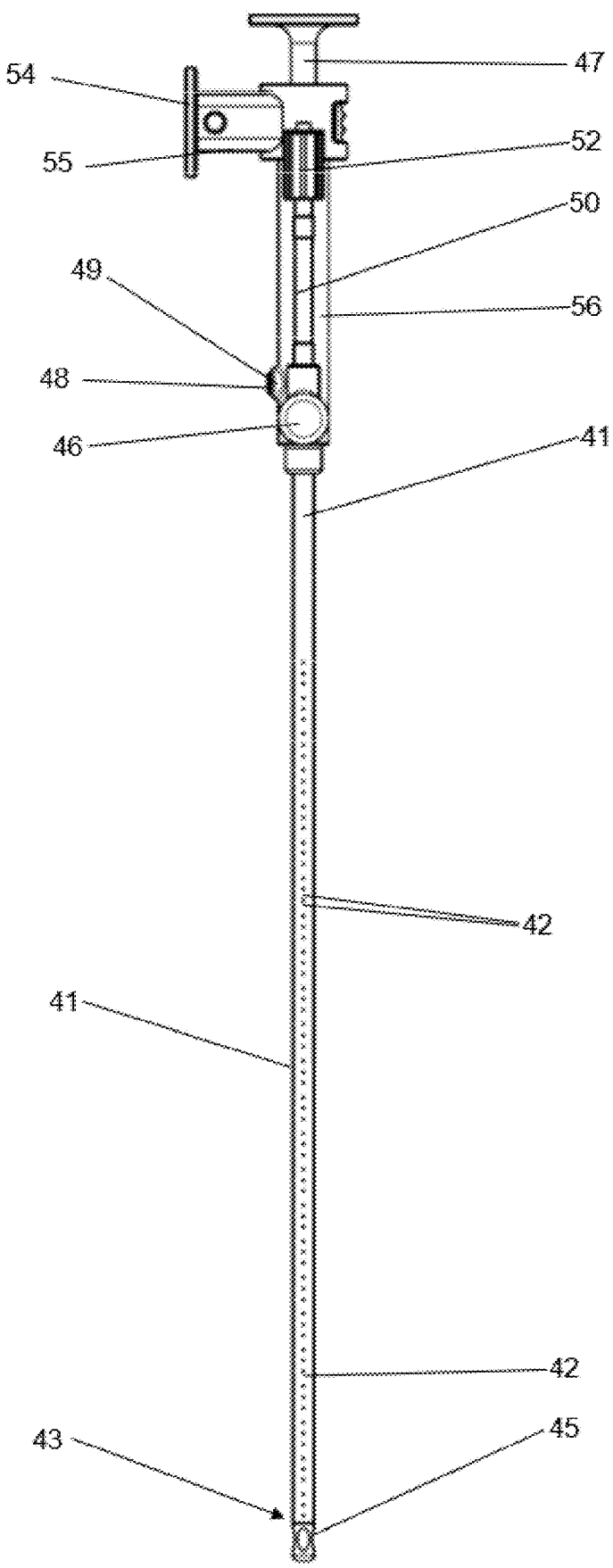
FIG. 3: illustrates a schematic view of an exemplary alternative third medical device according to one embodiment for local application of a fluid.
Figure 4:
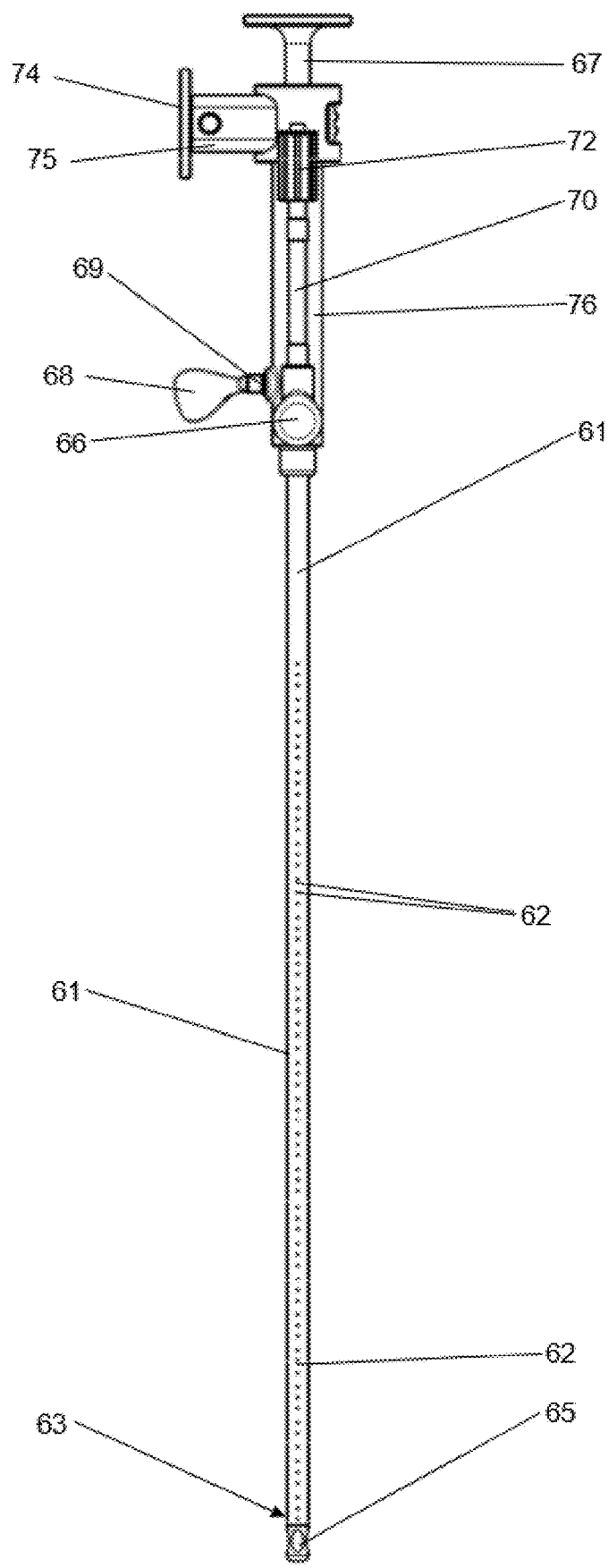
FIG. 4: illustrates a schematic view of an exemplary alternative fourth medical device according to one embodiment for local application of a fluid.
Figure 5:
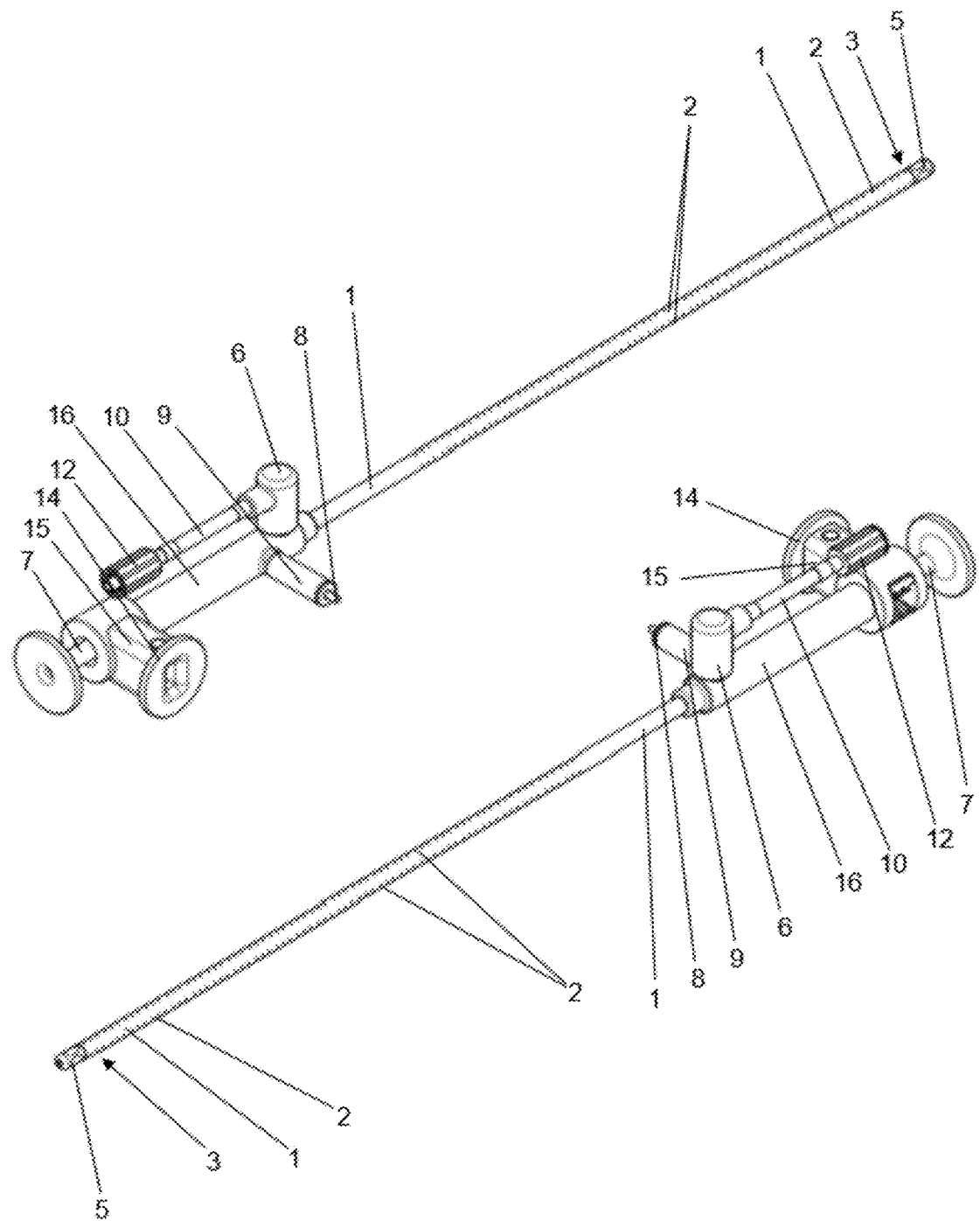
FIG. 5: illustrates two schematic perspective external views of the first device according to FIG. 1.
Figure 6:
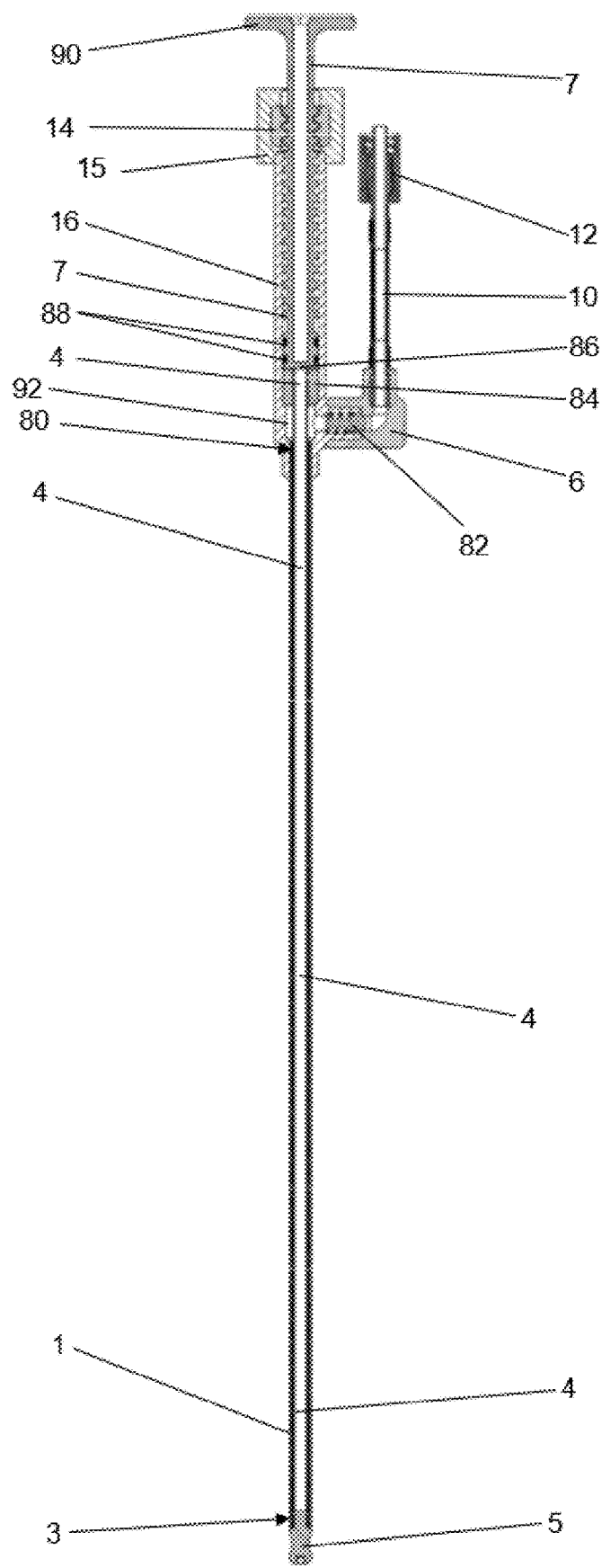
FIG. 6: illustrates a schematic longitudinal cross-sectional view of the first device according to FIGS. 1 and 5 in a starting state.
Figure 7:
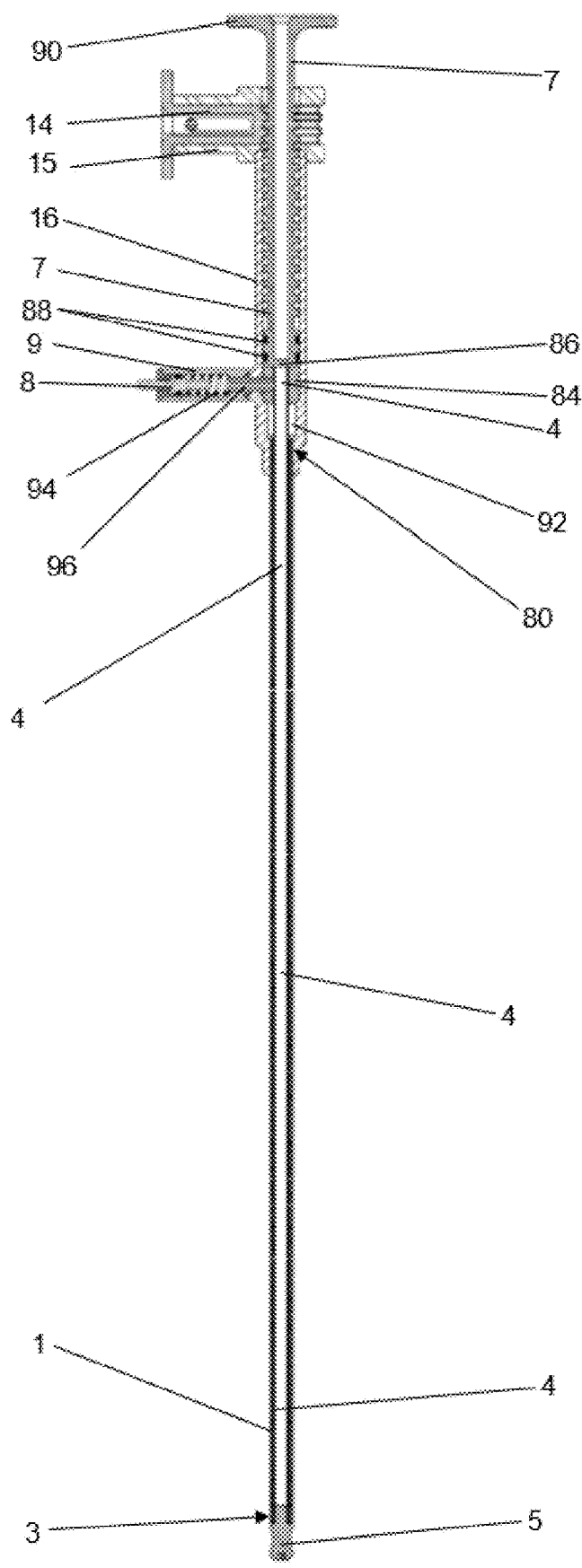
FIG. 7: illustrates a schematic longitudinal cross-sectional view of the first device according to FIGS. 1, 5, and 6 in the starting state, whereby the longitudinal cross-section extends perpendicular to the one according to FIG. 6.
Figure 8:
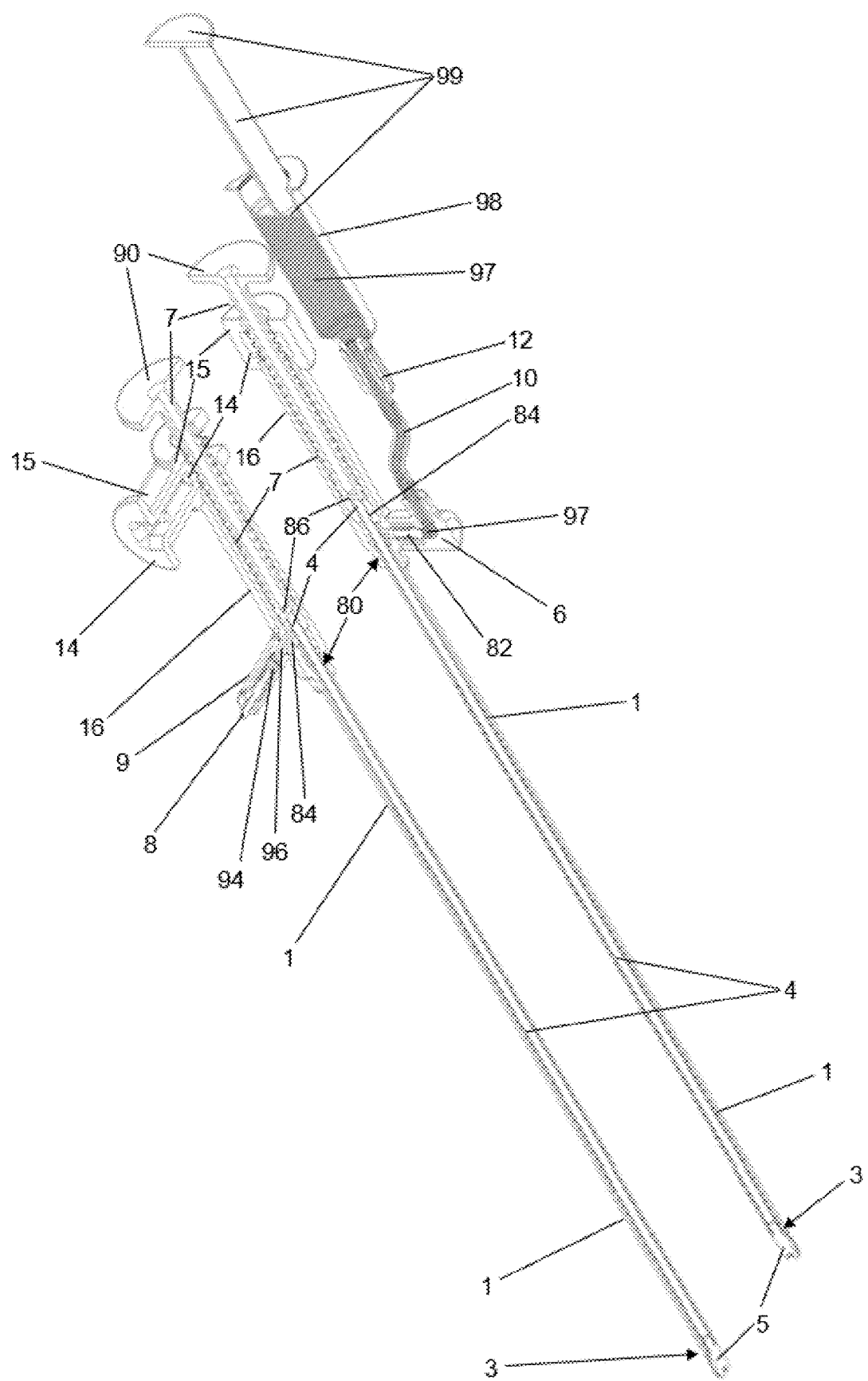
FIG. 8: illustrates two schematic perspective longitudinal cross-sectional views, sectioned perpendicular with respect to each other, of the first device according to FIGS. 1 and 5 to 7 with a syringe attached for injection of a fluid.

FIGS. 1 and 5 to 14 illustrate different depictions of a first exemplary device according to one embodiment. FIGS. 2, 3, and 4 illustrate three different exemplary embodiments. Referring to the first exemplary embodiment, FIGS. 8 to 14 illustrate the workflow of a method according to one embodiment that can be applied readily to the other exemplary embodiments according to FIGS. 2 to 4.

The first exemplary device illustrated in FIGS. 1 and 5 to 14 has, on the frontal distal side, an external hose 1, in which a multitude of openings 2 that extend through the hose wall are arranged. The external hose 1 consists of a plastically deformable material such that its shape can be adapted to the shape of a hollow space.

The external hose 1 is connected, on its distal first end 3, to an internal hose 4 that is coaxially arranged within the external hose 1. The internal hose 4 is not visualized in FIGS. 1 and 5, but is visible in the cross-sectional views of FIGS. 6 to 14. The internal hose 4 has an external diameter, which, in the relaxed state (see FIGS. 6 to 9 and 13 and 14), is at least equal in size to the internal diameter of the external hose 1. By this means, the internal hose 4, being in the relaxed state, closes the openings 2 in the external hose 1 on the internal side of the external hose 1. Moreover, no volume remains in the intervening space between the external hose 1 and the internal hose 4. The internal hose 4 and the external hose 1 jointly form a valve for opening and closing of the openings 2 in the external hose 1.

The internal hose 4 is connected to the external hose 1 by means of a connecting element 5. For this purpose, the connecting element 5 has a cylindrical projection with an external thread that is screwed into the open distal end of the internal hose 4. While the connecting element 5 is being screwed in, the external thread of the cylindrical projection cuts an internal thread into the internal wall of the internal hose 4. In this context, the internal hose 4 expands and is pressed onto the external hose 1, such that the intervening space between the external hose 1 and the internal hose 4 is closed in gas-tight and liquid-tight manner. Moreover, the connecting element 5 closes the internal hose 4 on its distal end in gas-tight and liquid-tight manner.

On a proximal second end 80 (see FIGS. 6 to 14), the external hose 1 is connected to a housing 16. The intervening space between the external hose 1 and the internal hose 4 is connected to a connector 6 through which a fluid 97 (see FIGS. 8 to 14) can be supplied into the intervening space. The housing 16 forms, on its inside, a swept volume for a thrust piston 7 that can be operated from outside the device. The swept volume for the thrust piston 7 is connected to the internal space of the internal hose 4. A liquid or a gas is present on the inside of the swept volume and of the internal hose 4. Increasing the swept volume by pulling out the thrust piston 7 from the housing 16 aspirates liquid or gas, at least partly, out of the internal hose 4 such that the hose walls of the internal hose 4 contract and the internal hose 4 can be transitioned into a radially contracted state (see FIGS. 10 to 12). The housing 16 with the swept volume and the thrust piston 7 jointly form a piston syringe that can be considered to be an operating element for changing the gas pressure or the volume of the liquid in the internal hose 4.

Moreover, an indicator is fastened to the housing 16 that can be used to read by eye from outside, whether the internal hose 4 is in the radially contracted state or in the expanded state. For this purpose, a pin 8 in a signalling colour is supported, as in a bearing, with limited axial mobility in a housing 9 for the pin 8. The colour of the housing 9 is preferred to contrast strongly the colour of the pin 8. If the pin 8 projects from the housing 9 for the pin 8, the internal hose 4 is in the expanded state. If the pin 8 is sunk into the housing 9 for the pin 8, the internal hose 4 is in the radially contracted state.

The connector 6 has a line 10 connected to it that connects the connector 6 to a connecting adapter 12, such as, for example, a Luer lock adapter.

Moreover, a lock 14 for locking the thrust piston 7 is arranged on the housing 16. For this purpose, the lock 14 is supported, as in a bearing, in a housing 15 for the lock 14 such as to be perpendicular to the direction of motion of the thrust piston 7. The thrust piston 7 includes, on its outside, a multitude of grooves on the external circumference that are engaged by matching strips of the lock 14, when the thrust piston 7 is locked (see FIGS. 6 to 8 and 10 to 14). Pulling the lock 14 out of the housing 15 for the lock 14 (see FIG. 9) unlocks the thrust piston 7 and allows it to be moved axially in the swept volume of the housing 16. One embodiment can provide the lock 14 to be supported appropriately, as in a bearing, by means of a compression spring (not illustrated) in the housing 15 for the lock 14 such that the lock 14 is being pushed onto the thrust piston 7 and locks it.

The second exemplary device according to one embodiment illustrated in FIG. 2 is identical to the first exemplary embodiment according to FIGS. 1 and 5 to 14 except for the pressure indicator missing. The second exemplary device according to one embodiment has, on the frontal distal side, an external hose 21, in which a multitude of openings 22 that extend through the hose wall are arranged. The external hose 21 consists of a plastically deformable material such that its shape can be adapted to the shape of a hollow space.

The external hose 21 is connected, on its distal first end 23, to an internal hose (not illustrated in FIG. 2) that is coaxially arranged within the external hose 21 or is connected to the internal wall of the external hose 21 along a connecting line, in one embodiment without covering the openings 22 along the connecting line in this context. The internal hose has an external diameter, which, in the relaxed state, is at least equal in size to the internal diameter of the external hose 21. By this means, the internal hose, being in the relaxed state, closes the openings 22 in the external hose 21 on the internal side of the external hose 21. Moreover, no volume remains in the intervening space between the external hose 21 and the internal hose. The internal hose and the external hose 21 jointly form a valve for opening and closing of the openings 22 in the external hose 21.

The internal hose is connected to the external hose 21 by means of a connecting element 25. For this purpose, the connecting element 25 has a cylindrical projection with an external thread that is screwed into the open distal end of the internal hose, or a cylindrical or conical projection with strips that push or cut themselves into the material of the internal hose. In this context, the internal hose expands and is pressed onto the external hose 21, such that the intervening space between the external hose 21 and the internal hose is closed in gas-tight and liquid-tight manner. Moreover, the connecting element 25 closes the internal hose on its distal end in gas-tight and liquid-tight manner.

The external hose 21 is connected to the housing 36 on a proximal second end of the external hose 21 that is arranged in the area of a connector 26 on the inside of a housing 36 and is not illustrated in FIG. 2. The intervening space between the external hose 21 and the internal hose is connected to the connector 26 such as to be through-going to a fluid (not illustrated in FIG. 2). Accordingly, the fluid can be supplied through the connector 26 into the intervening space. The housing 36 forms, on its inside, a swept volume for a thrust piston 27 that can be operated from outside the device. The swept volume for the thrust piston 27 is connected to the internal space of the internal hose. A liquid or a gas is present on the inside of the swept volume and of the internal hose. Increasing the swept volume by pulling out the thrust piston 27 from the housing 36 aspirates liquid or gas, at least partly, out of the internal hose such that the hose walls of the internal hose contract and the internal hose can be transitioned into a radially contracted state. By this means, the openings 22 in the external hose 21 can be opened and the valve formed by the internal hose and the external hose 21 with the openings 22 is operated and/or opened by this means. The housing 36 with the swept volume and the thrust piston 27 jointly form a piston syringe that can be considered to be an operating element for changing the gas pressure or the volume of the liquid in the internal hose.

The connector 26 has a line 30 connected to it that connects the connector 26 to a connecting adapter 32, such as, for example, a Luer lock adapter.

Moreover, a lock 34 for locking the thrust piston 27 is arranged on the housing 36. For this purpose, the lock 34 is supported, as in a bearing, in a housing 35 for the lock 34 such as to be perpendicular to the direction of motion of the thrust piston 27. The thrust piston 27 includes, on its outside, a multitude of grooves on the external circumference that are engaged by matching strips of the lock 34, when the thrust piston 27 is locked. Pulling the lock 34 out of the housing 35 for the lock 34 unlocks the thrust piston 27 and allows it to be moved axially in the swept volume of the housing 36. One embodiment can provide the lock 34 to be supported appropriately, as in a bearing, by a compression spring (not illustrated) in the housing 35 for the lock 34 such that the lock 34 is being pushed onto the thrust piston 27 and locks it.

The second exemplary embodiment according to FIG. 2 differs from the first exemplary embodiment according to FIGS. 1 and 5 to 14 in that no additional indicator is provided that could be used to read whether the internal hose is in the radially contracted state. Only the position of the thrust piston 27 can be used by the user to conclude whether the internal hose is in the radially contracted state and whether, thus, the openings 22 are opened, without an additional measurement for confirmation. The device according to the second exemplary embodiment is thus less expensive, but also less safe. This is sufficient for simple rinsing procedures, in which the hose system does not need to be implanted in a patient or the rest of the device can be changed easily in case of an implanted hose system.

The third exemplary device according to one embodiment illustrated in FIG. 3 is identical to the first exemplary embodiment according to FIGS. 1 and 5 to 14 except for the pressure indicator being different. The third exemplary device according to one embodiment has, on the frontal distal side, an external hose 41, in which a multitude of openings 42 that extend through the hose wall are arranged. The external hose 41 consists of a plastically or elastically deformable material such that its shape can be adapted, or self-adapts, to the shape of a hollow space.

The external hose 41 is connected, on its distal first end 43, to an internal hose (not illustrated in FIG. 3) that is coaxially arranged within the external hose 41 or is connected to the internal wall of the external hose 41 along a connecting line, in one embodiment without covering the openings 42 along the connecting line in this context. The internal hose has an external diameter, which, in the relaxed state, is at least equal in size to the internal diameter of the external hose 41. By this means, the internal hose, being in the relaxed state, closes the openings 42 in the external hose 41 on the internal side of the external hose 41. Moreover, no volume remains in the intervening space between the external hose 41 and the internal hose. The internal hose and the external hose 41 jointly form a valve for opening and closing of the openings 42 in the external hose 41.

The internal hose is connected to the external hose 41 by means of a connecting element 45. For this purpose, the connecting element 45 has a cylindrical projection with an external thread that is screwed into the open distal end of the internal hose, or a cylindrical or conical projection with strips that push or cut themselves into the material of the internal hose. In this context, the internal hose expands and is pressed onto the external hose 41, such that the intervening space between the external hose 41 and the internal hose is closed in gas-tight and liquid-tight manner. Moreover, the connecting element 45 closes the internal hose at its distal end in gas-tight and liquid-tight manner.

The external hose 41 is connected to the housing 56 on a proximal second end of the external hose 41 that is arranged in the area of a connector 46 on the inside of a housing 56 and is not illustrated in FIG. 3. The intervening space between the external hose 41 and the internal hose is connected to the connector 56 such as to be through-going to a fluid (not illustrated in FIG. 3). Accordingly, the fluid can be supplied through the connector 46 into the intervening space. The housing 56 forms, on its inside, a swept volume for a thrust piston 47 that can be operated from outside the device.

The swept volume for the thrust piston 47 is connected to the internal space of the internal hose. A liquid or a gas is present on the inside of the swept volume and of the internal hose. Increasing the swept volume by pulling out the thrust piston 47 from the housing 56 aspirates liquid or gas, at least partly, out of the internal hose such that the hose walls of the internal hose contract and the internal hose can be transitioned into a radially contracted state. By this means, the openings 42 in the external hose 41 can be opened and the valve formed by the internal hose and the external hose 41 with the openings 42 is operated and/or opened by this means. The housing 56 with the swept volume and the thrust piston 47 jointly form a piston syringe that can be considered to be an operating element for changing the gas pressure or the volume of the liquid in the internal hose.

Moreover, an indicator is fastened to the housing 56 that can be used to read by eye from outside whether the internal hose is in the radially contracted state or in the expanded state. For this purpose, a flexible membrane 48 in signalling colour is fastened axially to a connector 49 for the membrane 48. If the membrane 48 projects from the connector 49 for the membrane 48 such as to be convex, the internal hose is in the expanded state. If the membrane 48 is drawn into the connector 49 for the membrane 48 such as to be concave, the internal hose is in the radially contracted state.

The connector 46 has a line 50 connected to it that connects the connector 46 to a connecting adapter 52, such as, for example, a Luer lock adapter.

Moreover, a lock 54 for locking the thrust piston 47 is arranged on the housing 56. For this purpose, the lock 54 is supported, as in a bearing, in a housing 55 for the lock 54 such as to be perpendicular to the direction of motion of the thrust piston 47. The thrust piston 47 includes, on its outside, a multitude of grooves on the external circumference that are engaged by matching strips of the lock 54, when the thrust piston 47 is locked. Pulling the lock 54 out of the housing 55 for the lock 54 unlocks the thrust piston 47 and allows it to be moved axially in the swept volume of the housing 56. One embodiment can provide the lock 54 to be supported appropriately, as in a bearing, by a compression spring (not illustrated) in the housing 55 for the lock 54 such that the lock 54 is being pushed onto the thrust piston 47 and locks it.

The third exemplary embodiment according to FIG. 3 differs from the first exemplary embodiment according to FIGS. 1 and 5 to 14 in that a different indicator is provided that can be used to read whether the internal hose is in the radially contracted state.

The fourth exemplary device according to one embodiment illustrated in FIG. 4 is identical to the first exemplary embodiment according to FIGS. 1 and 5 to 14 except for the pressure indicator being different. The third exemplary device according to one embodiment has, on the frontal distal side, an external hose 61, in which a multitude of openings 62 that extend through the hose wall are arranged. The external hose 61 consists of a plastically or elastically deformable material such that its shape can be adapted, or self-adapts, to the shape of a hollow space.

The external hose 61 is connected, on its distal first end 63, to an internal hose (not illustrated in FIG. 4) that is coaxially arranged within the external hose 61. The internal hose has an external diameter, which, in the relaxed state, is at least equal in size to the internal diameter of the external hose 61. By this means, the internal hose, being in the relaxed state, closes the openings 62 in the external hose 61 on the internal side of the external hose 61. Moreover, no volume remains in the intervening space between the external hose 61 and the internal hose. The internal hose and the external hose 61 jointly form a valve for opening and closing of the openings 62 in the external hose 61.

The internal hose is connected to the external hose 61 by means of a connecting element 65. For this purpose, the connecting element 65 has a cylindrical projection with an external thread that is screwed into the open distal end of the internal hose, or a cylindrical or conical projection with strips that push or cut themselves into the material of the internal hose. In this context, the internal hose expands and is pressed onto the external hose 61, such that the intervening space between the external hose 61 and the internal hose is closed in gas-tight and liquid-tight manner. Moreover, the connecting element 65 closes the internal hose on its distal end in gas-tight and liquid-tight manner.

The external hose 61 is connected to the housing 76 on a proximal second end of the external hose 61 that is arranged in the area of a connector 66 on the inside of a housing 76 and is not illustrated in FIG. 4. The intervening space between the external hose 61 and the internal hose is connected to the connector 76 such as to be through-going to a fluid (not illustrated in FIG. 4). Accordingly, the fluid can be supplied through the connector 66 into the intervening space. The housing 76 forms, on its inside, a swept volume for a thrust piston 67 that can be operated from outside the device. The swept volume for the thrust piston 67 is connected to the internal space of the internal hose. A liquid or a gas is present on the inside of the swept volume and of the internal hose. Increasing the swept volume by pulling out the thrust piston 67 from the housing 76 aspirates liquid or gas, at least partly, out of the internal hose such that the hose walls of the internal hose contract and the internal hose can be transitioned into a radially contracted state. By this means, the openings 62 in the external hose 61 can be opened and the valve formed by the internal hose and the external hose 61 with the openings 62 is operated and/or opened by this means. The housing 76 with the swept volume and the thrust piston 67 jointly form a piston syringe that can be considered to be an operating element for changing the gas pressure or the volume of the liquid in the internal hose.

Moreover, an indicator is fastened to the housing 76 that can be used to read by eye from outside whether the internal hose is in the radially contracted state or in the expanded state. For this purpose, a flexible balloon 68 in signalling colour is fastened axially to a connector 69 for the balloon 68. The gas or liquid on the inside of the internal hose is contained in the balloon 68 and is connected to the balloon 68 such as to be through-going. When the balloon 68 expands and/or is inflated, the internal hose is in the expanded state. When the balloon 68 is compact or limp, the internal hose is in the radially contracted state.

The connector 66 has a line 70 connected to it that connects the connector 66 to a connecting adapter 72, such as, for example, a Luer lock adapter.

Moreover, a lock 74 for locking the thrust piston 67 is arranged on the housing 76. For this purpose, the lock 74 is supported, as in a bearing, in a housing 75 for the lock 74 such as to be perpendicular to the direction of motion of the thrust piston 67. The thrust piston 67 includes, on its outside, a multitude of grooves on the external circumference that are engaged by matching strips of the lock 74, when the thrust piston 67 is locked. Pulling the lock 74 out of the housing 75 for the lock 74 unlocks the thrust piston 67 and allows it to be moved axially in the swept volume of the housing 76. One embodiment can provide the lock 74 to be supported appropriately, as in a bearing, by a compression spring (not illustrated) in the housing 75 for the lock 74 such that the lock 74 is being pushed onto the thrust piston 67 and locks it.

The fourth exemplary embodiment according to FIG. 4 differs from the first exemplary embodiment according to FIGS. 1 and 5 to 14 in that a different indicator is provided that can be used to read whether the internal hose is in the radially contracted state.

FIGS. 6 to 14 allow the internal set-up and the working mechanism of the device according to the first exemplary embodiment according to one embodiment to be recognised. The working mechanism and the internal set-up are largely applicable and/or fully applicable, except for the functioning of the respective indicator, to the other exemplary embodiments according to FIGS. 2 to 4. The workflow of a method according to one embodiment shall be described in the following in exemplary manner based on the first device according to one embodiment.

The proximal second end 80 of the external hose 1 is connected, on its outside, to the housing 16 in liquid-tight manner. A non-return valve 82 is arranged on the inside of the connector 6 and is pushed against a valve seat on the inside of the connector 6 by means of a spring. The non-return valve 82 prevents any backflow of the fluid 97 out of the housing 16 into the line 10. The proximal end of the internal hose 4 is affixed in the housing 16 by means of a sleeve 84 and is closed by this means in gas-tight and liquid-tight manner. The proximal end of the internal hose 4 is guided out of the proximal second end 80 of the external hose 1 and projects from the external hose 1 inside the housing 16. The proximal end of the internal hose 4 and the sleeve 84 jointly form a limit stop for the thrust piston 7. In FIGS. 6 to 9 and 13 and 14, a distal thrust surface 86 of the thrust piston 7 touches against the limit stop in flush-mounted manner such that the entire liquid or the entire gas is contained in the internal space of the internal hose 4 and in the indicator. The liquid or the gas, which can also be considered to be a second fluid, push onto the internal wall of the internal hose 4 in this context and thus keep it in the expanded state. The thrust piston 7 is sealed with respect to the swept volume in the housing 16 by means of two circumferential seals 88 such that no gas or no liquid can escape between the thrust piston 7 and the internal wall of the housing 16. The proximal end (on the top in FIGS. 1 to 4 and 6 and 7, on the top left in FIGS. 8, 11, and 13, on the left in FIGS. 9, 10, 12, and 14) of the thrust piston 7 has a handle part 90 arranged on it by means of which the thrust piston 7 can be pushed into the housing 16 and drawn from the housing 16 by hand, provided the thrust piston 7 is not locked by the lock 14.

The connector 6 terminates in the housing 16 between the sleeve 84 and the proximal end 80 of the external hose 1. In this place, the housing 16, on its inside, and the internal hose 4, the sleeve 84, and the external hose 1 jointly form the boundary of a hollow space 92 that is bounded on its proximal side by the sleeve 84 and is essentially bounded on its distal side by the proximal end 80 of the external hose 1. The fluid can be pressed in distal direction from the hollow space 92 into the intervening space between the internal hose 4 and the external hose 1, when the internal hose 4 is in the radially contracted state.

The pressure indicator is connected, on its inside, to the internal space of the internal hose 4 by means of a channel 96. For this purpose, the pin 8 is arranged in a chamber of the housing 9 of the pin 8, whereby the chamber is connected to the channel 96 in liquid-permeable or gas-permeable manner. The pin 8 is supported, as in a bearing, by means of a spring 94 such that it is being pushed out of the housing 9 for the pin 8. The pin 8 is sealed with respect to the housing 9 of the pin 8 in this context. In the radially contracted state of the internal hose 4, the pin 8 is pulled into the housing 9 against the force of the spring 94. Otherwise, the pin 8 projects from the housing 9. This makes it easy to recognise from outside whether the internal hose 4 is in the contracted or in the expanded state. By this means, a possible malfunction of the thrust piston 7 and thus of the device becomes recognisable to the user.

The fluid 97 can be injected into the connector 6 via a syringe 98 with the aid of a syringe piston 99. For this purpose, the syringe 98 containing the fluid 97 is being connected to the connecting adapter 12. The pressure applied to the fluid 97 by the syringe piston 99 opens the non-return valve 82 against its compression spring, and the fluid 97 flows through the connector 6 into the hollow space 92 in the housing 16. The internal hose 4, being in the expanded state, seals the external hose 1 with respect to the internal hose 4 (see FIG. 8). By this means, the fluid 97 can initially not advance between the external hose 1 and the expanded internal hose 4.

Figure 9:
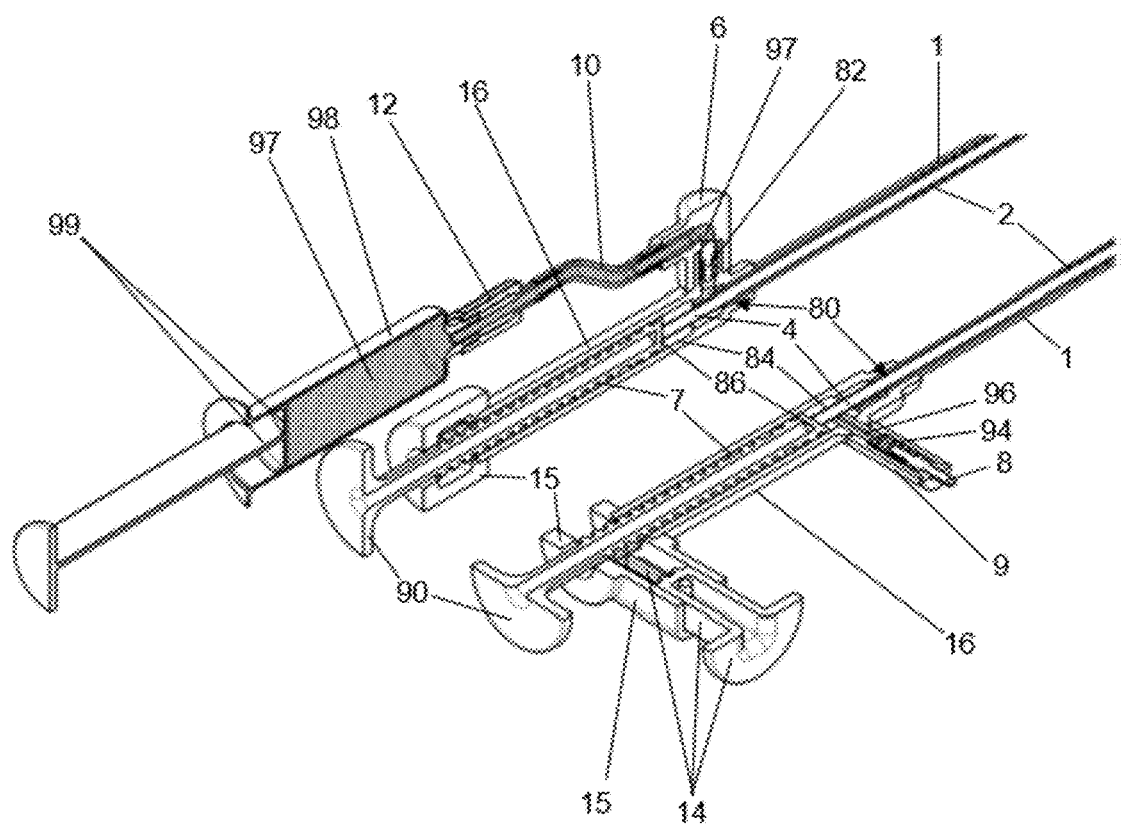
FIG. 9: illustrates a detail magnification of the longitudinal cross-sectional views according to FIG. 8 with unlocked thrust piston.
Figure 10:
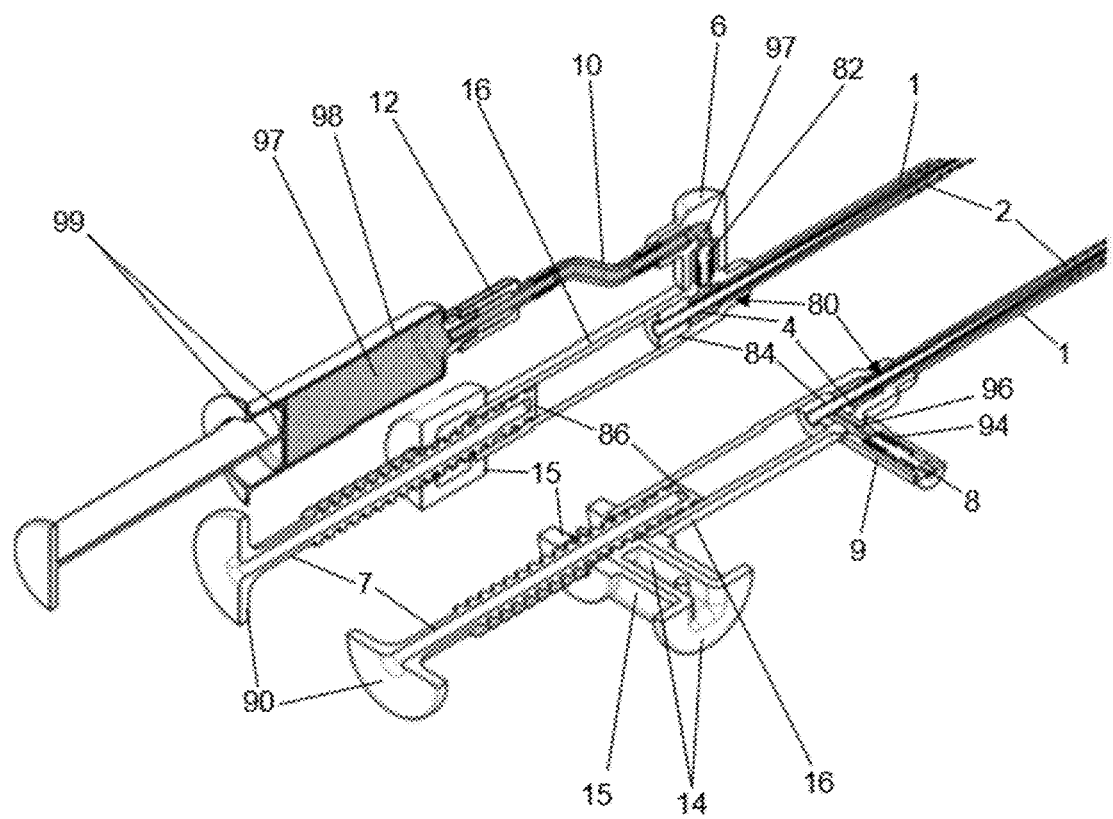
FIG. 10: illustrates a detail magnification of two schematic perspective longitudinal cross-sectional views, sectioned perpendicular with respect to each other, of the first device according to FIGS. 1 and 5 to 9, whereby the openings in the external hose are opened by retracting the thrust piston.

Initially, the lock 14 is detached by pulling out the lock 14 from the housing 15 of the thrust piston 7 (see FIG. 9). Subsequently, the thrust piston 7 is pulled in proximal direction by means of the handle 90 in order to open the intervening space between the external hose 1 and the internal hose 4 as well as the through-going openings 2 in the hose wall of the external hose 1. As a result, gas or liquid flows from the inside of the internal hose 4 into the swept volume of the thrust piston 7 on the inside of the housing 16. The internal hose 4 is thus transitioned into the radially contracted state and the openings 2 and the intervening space between the external hose 1 and the internal hose 4 are opened in this context proceeding from the hollow space 92. The thrust piston 7 is locked by sliding the lock 14 into the housing 15 such that the thrust piston 7 is not being pulled into the swept volume of the housing 16 again due to the elastic force saved in the internal hose 4 through the deformation thereof (see FIG. 10). Accordingly, having the lock 14 prevents the radially contracted state from transitioning by itself into the relaxed expanded state. Theoretically, it is also feasible to use the radially contracted state as the relaxed state. However, it is preferred to have the expanded state be the relaxed state, because the openings 2 are or will be closed upon any leakage of the swept volume, internal hose 4 or indicator. The radially contracted state of the internal hose 4 thus obtained can be recognised in that the pin 8 is drawn into and/or retracted into the housing 9 of the pin 8.

Figure 11:
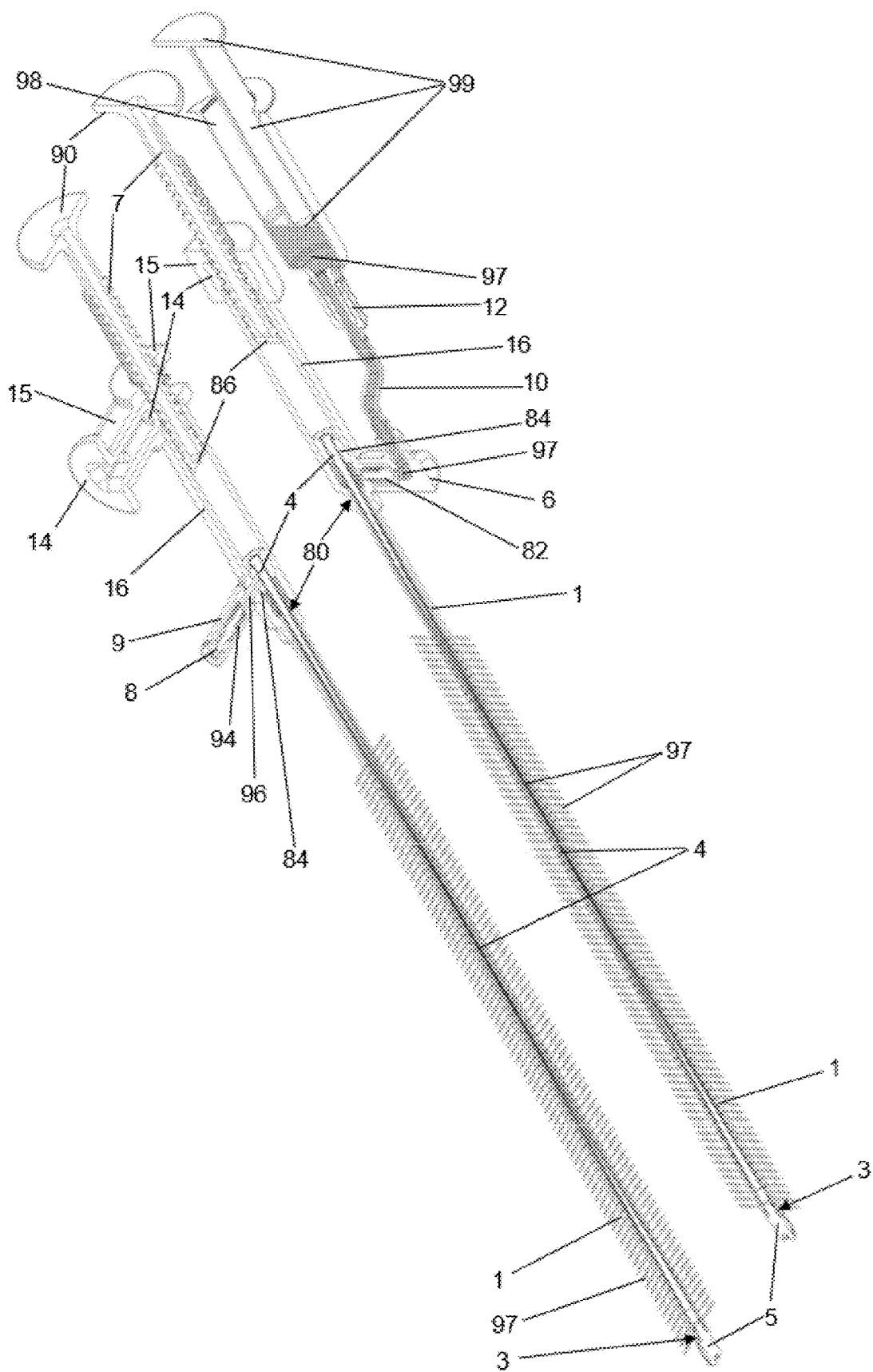
FIG. 11: illustrates two schematic perspective longitudinal cross-sectional views, sectioned perpendicular with respect to each other, of the first device according to FIGS. 1 and 5 to 10 during the application of the fluid through the opened openings.
Figure 12:
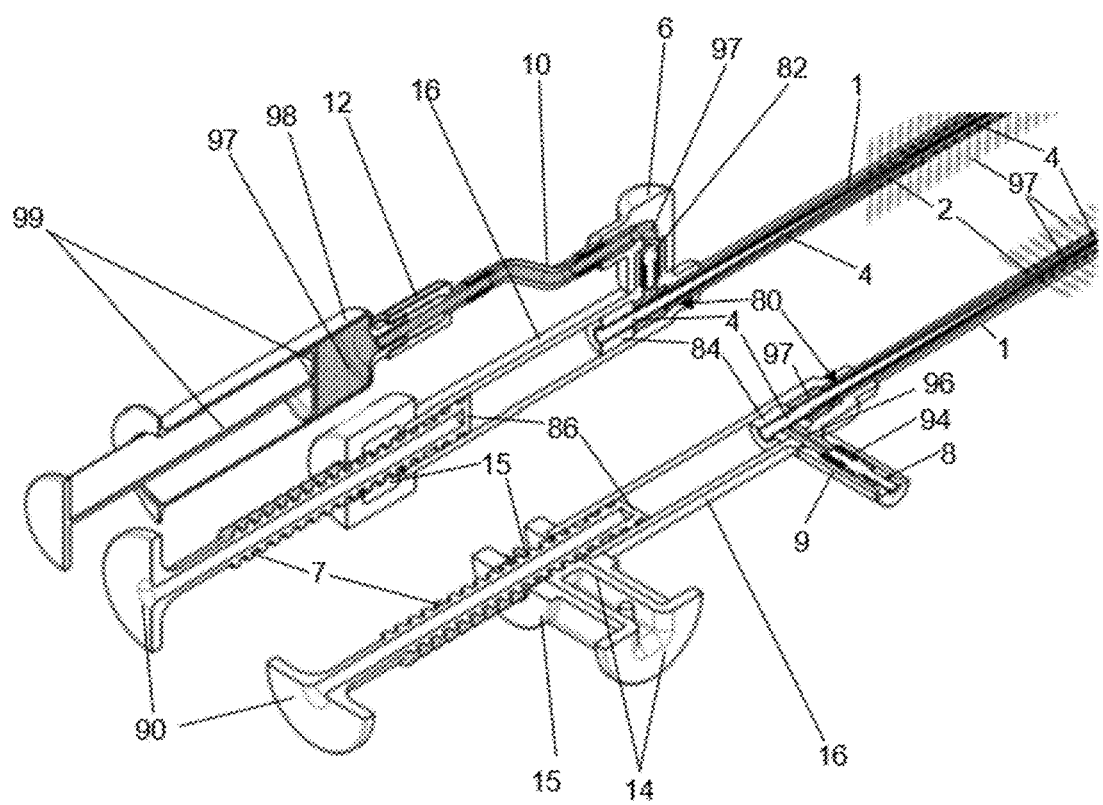
FIG. 12: illustrates a detail magnification of the longitudinal cross-sectional views according to FIG. 11.

After the intervening space and the openings 2 are opened, the syringe is used to press the fluid 97 through the intervening space between the external hose 1 and the internal hose 4 and to push it from there out of the openings 2 (see FIGS. 11 and 12). The sum of the free cross-sections of the openings 2 is smaller than the free cross-section of the intervening space such that the pressure of the fluid 97 is still sufficient, even at the most distally arranged openings 2 that are situated in the area of the connecting element 5, such that the desired dispensation of fluid 97 takes place in this area as well. Accordingly, the individual openings 2 in one embodiment must have very small free cross-sections as their number is large (in one embodiment more than one hundred). For example, for an internal diameter of the internal hose of approximately 5 mm and an external diameter of the internal hose 4 of approximately 1.5 mm, the openings 2 can be circular, through-going cylindrical holes with a diameter between 10 µm to 50 µm.

After a desired quantity of the fluid 97 is supplied through the openings 2, the intervening space and the openings 2 are closed again by expanding the internal hose 4 by detaching the lock 14 and pushing the thrust piston 7 into the housing 16 again. The portions of the fluid still remaining in the intervening space between the external hose 1 and the internal hose 4 are pushed through the openings 2 in this process. This process can be repeated until the syringe no longer contains any fluid 97. Then the syringe must be replaced, if applicable.

Figure 13:
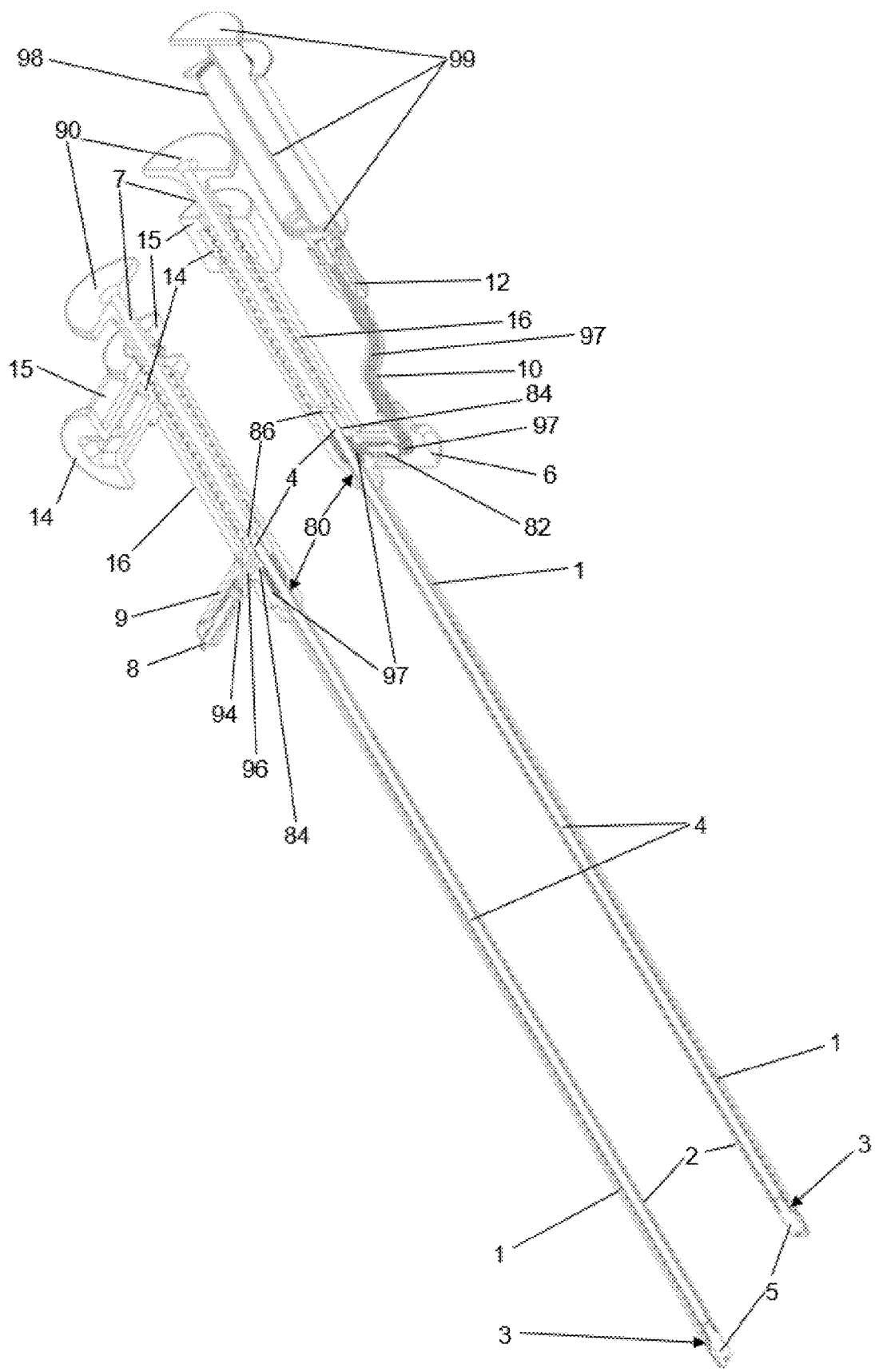
Figure 14:
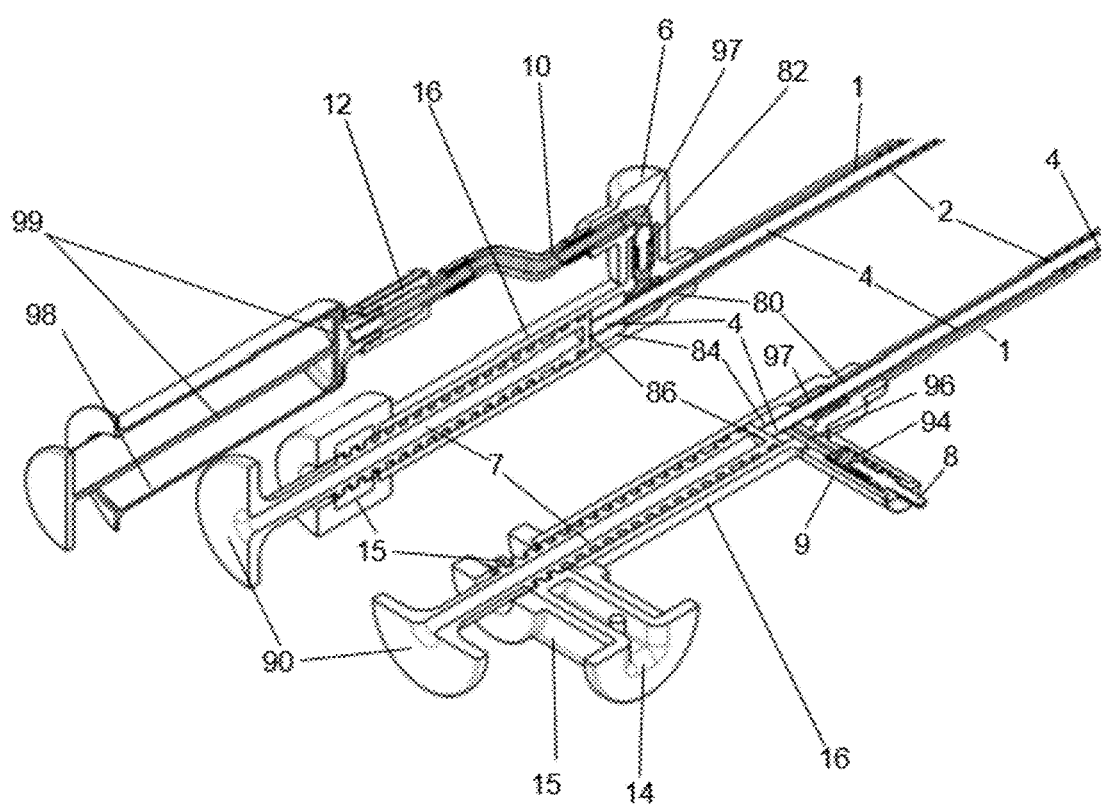
FIG. 14: illustrates a detail magnification of the longitudinal cross-sectional views according to FIG. 13.

Accordingly, when the syringe is empty, the internal hose 4 is being transitioned into the expanded state again (see FIGS. 13 and 14). The syringe can then be removed or, if desired, can be replaced by a full syringe filled with the same fluid 97 or a different fluid. By this means, it is feasible to vary the treatment or rinsing process.

During the switch from the radially contracted state into the expanded state and vice versa, the external hose 1 is exposed to only a very small force such that it retains its external shape and in particular its length largely or fully unchanged. As a result, the rinsing takes place at the desired sites. During an implantation of the hose system, the adjoining tissue is not exposed to mechanical stress such that irritation of the inflamed tissue can be prevented. Moreover, closing the openings 2 prevents tissue from growing into the intervening space between the external hose 1 and the internal hose 4 and from engaging undercuts during extended indwelling times, and thus prevents injuries or undesired irritation of the recently treated tissue during the removal of the hose system.

Before use of the device, the device can be adapted to the hollow space to be rinsed by suitable plastic deformation of the hose system comprising the external hose 1 and the internal hose 4. However, the hose system and the device are particularly characterised in that the length of the hose system can be easily adapted to the hollow space to be rinsed or treated. The hose system can simply be cut off at the desired length on the distal side before use. The connecting element 5 is being unscrewed from the cut-off part of the internal hose 4 and is screwed in again into the distal end of the internal hose 4 generated by the cut. By this means, the internal hose 4 and the external hose 1 are tightly closed and connected to each other again on their distal ends.

The devices according to one embodiment are used for application of fluids 97 by first removing the fluid or the gas, at least in part, from the internal hose 4 by actuating the negative pressure-generating device, i.e. by pulling the thrust piston 7, 27, 47, 67 out of the housing 16, 36, 56, 76. In the process, the internal hose 4 collapses and a hollow space arises between the external side of the internal hose 4 and the internal side of the external hose 1, 21, 41, 61. The at least one opening 2, 22, 42, 62 in the jacket surface of the external hose 1, 21, 41, 61 is being exposed. Then, the fluid 97 to be applied is pressed via the connector 6, 26, 46, 66 into the intervening space between the internal hose 4 and the external hose 1, 21, 41, 61. Advantageously, the pressing process can be effected with a common plastic syringe in this context. The fluid 97 to be applied flows through the intervening space and then the fluid 97 exits through the openings 2, 22, 42, 62 of the external hose 1, 21, 41, 61 into the surroundings. After completed application of a sufficient quantity of the fluid 97, the negative pressure-generating device (the thrust piston 7) is being reset such that an equilibrium between the external pressure of the surroundings and the internal pressure of the fluid or gas in the internal hose 4 becomes established. Due to its restoring force, the elastic internal hose 4 relaxes into its starting shape and closes the openings 2, 22, 42, 62 in the external hose 1, 21, 41, 61. This process can basically be repeated any number of times.

After the device is shortened, the connecting element 5, 25, 45, 65 can be screwed or plugged easily into the distal (first) hose end of the internal hose 4 by the medical user. By this means, on the one hand, the internal hose 4 is being closed and concurrently the internal hose 4 expanded by the connecting element 5, 25, 45, 65 presses against the internal wall of the external hose 1, 21, 41, 61 such that the internal hose 4 is being clamped against the external hose 1, 21, 41, 61 and the intervening space between the internal hose 4 and the external hose 1, 21, 41, 61 is being closed.

Depending on the application, for example a disinfecting liquid or an aqueous solution comprising at least one antibiotic can be used as the fluid 97 to be applied.

For a medical application of the devices, the hoses 1, 4, 21, 41, 61, and in one embodiment the connecting elements 5, 25, 45, 65 as well, can be made up of biocompatible materials that contain radiopaquers such that the position of the external hose 1, 21, 41, 61 and, if applicable, of the connecting element 5, 25, 45, 65 can be determined by X-ray imaging procedures.

The features of the embodiments disclosed in the preceding description and in the claims, figures, and exemplary embodiments, can be essential for the implementation of the various embodiments both alone and in any combination.

Although specific embodiments have been illustrated and described herein, it will be appreciated by those of ordinary skill in the art that a variety of alternate and/or equivalent implementations may be substituted for the specific embodiments illustrated and described without departing from the scope of the present embodiments. This application is intended to cover any adaptations or variations of the specific embodiments discussed herein. Therefore, it is intended that these embodiments be limited only by the claims and the equivalents thereof.

The invention claimed is:

1. A medical device for local application of a fluid, comprising:
a flexibly deformable external hose with a hose wall, wherein the external hose comprises multiple through-going openings in the hose wall, wherein at least one of the multiple through-going openings is arranged in an area of a first end of the external hose;
a flexible internal hose, wherein at least sections of the internal hose are arranged on an inside of the external hose, where by the internal hose, in an relaxed state, has an external diameter that is at least equal to an internal diameter of the external hose, such that the internal hose, in the relaxed state, closes the multiple through-going openings of the external hose on an internal side of the external hose, wherein the external diameter of the internal hose can be transitioned from the relaxed state into a radially contracted state, in which the internal hose has a smaller external diameter, such that the multiple through-going openings are being exposed;
a connection that firmly connects the external hose and the internal hose to each other on the first end of the external hose, and closes the internal hose and the external hose in fluid-tight manner; and
a connector for supplying the fluid into intervening space between the internal side of the external hose and an external side of the internal hose, wherein the connector is arranged in an area of a second end of the external hose, wherein the second end of the external hose is situated opposite from the first end of the external hose;
wherein the internal hose remains in the relaxed state when no force is applied such that the multiple through-going openings are closed and wherein the internal hose is configured to be transferred to the radially contracted state by the action of force, thereby providing access to the multiple through-going openings.

2. The device of claim 1, wherein the internal hose can be transitioned into the radially contracted state through the generation of a negative pressure on an inside of the internal hose or through a volume reduction of a liquid on the inside of the internal hose.

3. The device of claim 1, wherein the internal hose is guided through a closure of the external hose on the second end of the external hose or through the hose wall of the external hose in the area of the second end.

4. The device of claim 1, wherein the device comprises an operating facility, wherein the operating facility comprises a piston syringe, a pump or a pipetting ball, and is further configured to transition the internal hose inside the external hose from the relaxed state into the radially contracted state such that the multiple through-going openings in the external hose are open.

5. The device of claim 1, wherein the connection is implemented by a connecting element.

6. The device of claim 1, wherein the intervening space between the external hose and the internal hose on the second end of the external hose is closed in fluid-tight manner.

7. The device of claim 1, wherein the first end of the external hose surrounds the internal hose.

8. The device of claim 1, wherein the internal hose contains a gas, wherein the internal hose can be transitioned into the radially contracted state by reducing a pressure of the gas in the internal hose, and can be transitioned again into the relaxed state by again supplying the gas or an additional gas, or
wherein a liquid fills the internal hose, wherein the internal hose can be transitioned into the radially contracted state by aspirating a portion of the liquid from the internal hose and can be transitioned again into the relaxed state by again supplying the liquid or another liquid into the internal hose.

9. The device of claim 1, wherein the internal side of the external hose and the external side of the internal hose jointly form a valve.

10. The device of claim 1, wherein all, or pairs or groups of the multiple through-going openings are situated at a distance from each other in an axial direction of the external hose.

11. The device of claim 1, wherein water, a physiological saline solution, a Ringer solution, or air are arranged on an inside of the internal hose, wherein the internal hose can be transitioned into the radially contracted state by reducing a pressure of the air or a volume of the water, the physiological saline solution or the Ringer solution.

12. The device of claim 1, wherein an indicator is connected to the internal hose that can be read from outside the device and indicates, whether the internal hose is in the relaxed state or in the contracted state, and wherein the indicator is a negative pressure indicator that is connected to the internal hose in a gas-permeable manner.

13. The device of claim 1, wherein at least one metal wire or at least one metal coil is arranged in a wall of the internal hose, and wherein the at least one metal wire or the at least one metal coil is arranged along the entire length of the internal hose.

14. The device of claim 1, wherein a non-return valve is arranged in the connector or in a connection of the connector to the intervening space between the external hose and the internal hose, wherein the non-return valve is configured to prevent the fluid from flowing out of the intervening space into the connector or out of the connector.

15. A hose system for designing the device according to claim 1.

16. A method for operating the device according to claim 1, comprising:
   A) transitioning the internal hose from the relaxed state into the contracted state, wherein the multiple through-going openings in the external hose are thus being opened; and
   B) supplying the fluid into the intervening space between the external hose and the internal hose.

\* \* \* \* \*